United States Patent [19]

Gerard-Monnier et al.

[11] Patent Number: 5,726,063
[45] Date of Patent: Mar. 10, 1998

[54] METHOD OF COLORIMETRIC ANALYSIS OF MALONIC DIALDEHYDE AND 4-HYDROXY-2-ENALDEHYDES AS INDEXES OF LIPID PEROXIDATION, KITS FOR CARRYING OUT SAID METHOD, SUBSTITUTED INDOLES FOR USE IN SAID METHOD AND THEIR PREPARATION

[75] Inventors: Dominique Gerard-Monnier, Vitry Sur Seine; Irène Erdelmeier, Paris; Jean Chaudiere, Saint Maur Des Fosses; Jean-Claude Yadan, Paris, all of France

[73] Assignee: Oxis Isle of Man, Limited, Portland, Oreg.

[21] Appl. No.: 702,197

[22] Filed: Aug. 23, 1996

Related U.S. Application Data

[63] Continuation of Ser. No. 362,418, filed as PCT/FR94/00530 May 6, 1994 published as WO94/27155 Nov. 24, 1994, abandoned.

[30] Foreign Application Priority Data

May 6, 1993 [FR] France .................... 93 05430

[51] Int. Cl.$^6$ ................. G01N 33/52; C07D 209/04
[52] U.S. Cl. ................. 436/128; 436/127; 436/166; 548/427; 548/452; 548/465; 548/466; 548/469; 548/509; 548/511; 548/517; 548/518
[58] Field of Search .................. 436/127, 128, 436/166; 548/427, 452, 465, 466, 469, 509, 511, 517, 518

[56] References Cited

U.S. PATENT DOCUMENTS

| | | | |
|---|---|---|---|
| 3,012,040 | 12/1961 | Lind et al. ................. | 548/493 |
| 3,903,108 | 9/1975 | Krutak ................. | 548/503 |
| 4,471,055 | 9/1984 | Opp ................. | 436/128 |
| 4,522,808 | 6/1985 | Jacquet et al. ................. | 424/59 |
| 5,188,935 | 2/1993 | Leif et al. ................. | 435/7.24 |

FOREIGN PATENT DOCUMENTS 55-151505 11/1980 Japan.

OTHER PUBLICATIONS

R.B. Carlin et al. *J. Am. Chem. Soc.* 1948, 70, 3421–3424.
R.B. Carlin et al. *J. Am. Chem. Soc.* 1957, 79, 934–941.

(List continued on next page.)

*Primary Examiner*—Arlen Soderquist
*Attorney, Agent, or Firm*—Jacobson, Price, Holman & Stern, PLLC

[57] ABSTRACT

A colorimetric assay of enaldehydes or of malonic dialdehyde as lipid peroxidation indices in an aqueous medium including a) addition to the medium of a reagent of a compound of general formula I and their optional addition salts with organic or inorganic bases or with organic or inorganic acids.

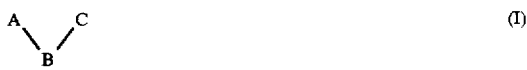

in which formula:
A and C, which may be identical or different, each represent H,

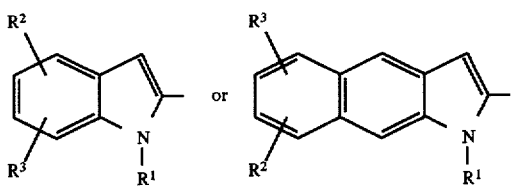

wherein
A and C cannot simultaneously represent H, with:

$R^1$=H; alkyl; aralkyl; aryl substituted on the aryl ring; alkyl sulfonate $Y^+$; alkyl phosphonate, $Y^+$; or alkyl carboxylate, $Y^+$;

$R^2$=H; —$OR^4$; F; Cl; Br; I; —$NO_2$; $SO_3^{31}$ $Y^+$; —CN; —$COOR^4$; or —$CONR^5R^6$;

$R^3$=H; —$OR^4$; —$NR^5R^6$; —$SR^4$; F; Cl; Br; I; —$NO_2$; —$SO_3$—$Y^+$; —CN; —$COR^5$; —$COOR^4$; or —$CONR^5R^6$;

$R^4$=H; alkyl; aralkyl; or aryl substituted on the aryl ring;

$R^5$=H; alkyl; aralkyl; or aryl substituted on the aryl ring;

$R^6$=H; aryl, aralkyl; or aryl substituted on the aryl ring;

$Y^+$=cation of an organic or inorganic base;

B =

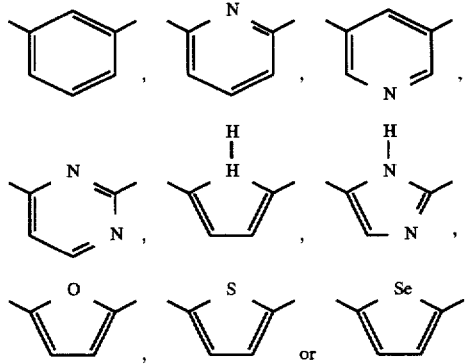

wherein alkyl represents a linear or branched group comprising 1 to 6 carbon;
aryl is substituted on the aryl ring with one or more groups which may be identical or different selected from $C_{1-6}$ alkyl, alkoxy, hydroxy, amino and carboxyl;

b) acidification of the medium; and
c) incubation of the acidified medium.

Requisites or kits for the implementation of the process are also disclosed.

21 Claims, 4 Drawing Sheets

OTHER PUBLICATIONS

E. Benier *Chem. Abstr.* 1958, 52, 13277g.
R.B. Carlin et al. *J. Am. Chem. Soc.* 1959, 81, 4673–4682.
M.J. Kamlet et al. *J. Org. Chem.* 1961, 26, 220–225.
M. Colonng et al. *Gazz. Chim. Ital.* 1962, 92, 1401–1421.
E. Sawicki et al. *Anal. Chem.* 1963, 35, 199–205.
N.P. Buu–Hoi et al. *J. Hetercycl. Chem.*, 1965, 2, 7–10.
J.G. Hiriyakkanavar et al. *Chem. Abstr.* 1966, 64, 11151g.
D.L. Horrocks *J. Chem. Phys.* 1968, 49, 2913–2917.
P. DeCointet et al. *Chem. Abstr,* 1977, 86, 139740k.
S. Plescia et al. *J. Hetercycl. Chem.* 1979, 16, 805–806.
S. Saleha et al. *Indian J. Chem.* 1979, 17B, 636.
V. Bocchi et al. *J. Chem. Soc. Chem. Commun.* 1983, 1074–1075.
W. Tao et al. *Chem. Abstr.* 1983, 99, 53886u.
M.M. Baradarani et al. *J. Chem. Soc. Perkin Trans.1* 1985, 1503–1508.

M. Vander Auweraer et al. *J. Phys. Chem.* 1986, 90, 1169–1175.
T. Sakamoto et al. *Heterocycles* 1986, 24, 1845–1847.
R.P. Thummel et al. *J. Org. Chem.* 1989, 54, 1720–1725.
W. Tao et al. *Chem. Abstr.* 1987, 107, 197992g.
V.I. Terenin et al. *Chem. Abstr.* 1991, 114, 121945t.
Free Radical Biology & Medicine, vol. 9, No. 6, Juin 1990, New York, NY, US pp. 515–540.
Methods in Enzymology, vol. 186, 1990, San Diego, CA, US pp. 407–421.
Methods in Enzymology, vol. 186, 1990, San Diego, CA, US pp. 421–431.
Journal of the Chemical Society (C), vol. 1971, 1971, Letchworth GB pp. 2606–2609.
Chemical Abstracts, vol. 74, No. 23, 7 Juin 1971, Columbus, Ohio, US; abstract No. 125326.

Kinetics of the formation of the adduct of tetramethoxypropane (TMP) with 1-methyl-2-phenylindole (MPI)

Calibration curve with tetramethoxypropane

Calibration curve with 4-hydroxynonenal diethyl acetal

Calibration curve in the presence of hydrochloric acid

METHOD OF COLORIMETRIC ANALYSIS OF MALONIC DIALDEHYDE AND 4-HYDROXY-2-ENALDEHYDES AS INDEXES OF LIPID PEROXIDATION, KITS FOR CARRYING OUT SAID METHOD, SUBSTITUTED INDOLES FOR USE IN SAID METHOD AND THEIR PREPARATION

This is a continuation of application Ser. No. 08/362,418, filed as PCT/FR94/00530 on May 6, 1994 published as WO94/27155 on Nov. 24, 994, which was abandoned upon the filing hereof.

The subjects of the invention are a process for the colorimetric assay of malonic dialdehyde (1,3-propanedial or MDA) and 4-hydroxy-2-enaldehydes which are formed in the course of the lipid peroxidation process, by means of compounds of substituted indole type, requisites or kits for the implementation of this process, new indole derivatives which may be used as reagents in the implementation of this process and their preparation.

In the prior art of the preparation of substituted indoles, it is known by document U.S. Pat. No. 4,522,808 compositions aimed to act against sunburns, containing 2-phenylindole derivatives which may have a multitude of meanings, notably by the fact that on the indole ring, it may be up to 6 substituents $R^1$ to $R^7$. Besides, on the benzenic part of the indole, substituents $R^4$ to $R^7$ may have several meanings and in particular represent an alkoxy radical from 1 to 4 carbon atoms or a carboxyalkyl radical which in fact is a carboxyalkylene group of formula $(CH_2)_n COOH$.

In the present invention, it may be used new 2-arylindole derivatives such as for instance 2-phenylindole derivatives which are nevertheless different from those described in this prior art reference, in particular by the fact that the substituent of the phenyl part of the indole ring can represent neither an alkoxy nor an alkyl radical nor a carboxylic alkylene radical.

On the other hand, document J. Chem. Soc. (C 1971, pages 2606–2608) describes 2-arylindole derivatives, in particular dimethylated or trimethylated indole derivatives, derivatives which are different from those subject matter of the present invention.

Finally, document Chemical Abstracts, volume 74,971, page 444, abstract 125326v, describes compounds for which $R^2=OCH_3$ and $R^3=$methyl, compounds which are different from those subject matter of the present invention.

In certain pathological states such as, for example, pre-eclampsia, myocardial infarction and states of shock, the oxidation of circulating lipoproteins or of certain cell membranes leads to the formation of lipid peroxides which decompose. The pathological states concerned may be demonstrated, or their evolution may be followed, by virtue of the assay of the decomposition products of these peroxidized unsaturated fatty acids.

The expression "lipid peroxidation" as used here collectively targets reaction routes which lead to the formation of hydroperoxides, dialkyl peroxides and endoperoxides of polyunsaturated fatty acids (PUFA) or their esters (in particular phospholipids, cholesteryl esters and mono-, di- and triglycerides), as well as to their decomposition.

The formation of "lipid peroxides" may be of non-enzymatic origin: spontaneous oxidation in the presence of oxygen in the elemental state, addition of singlet oxygen, oxidation catalysed by transition metal complexes or by partially degraded metalloproteins such as, for example, ferrihemoglobin, ferrimyoglobin or hematin, in the presence or absence of hydroperoxides formed beforehand.

This formation may also be of enzymatic origin, that is to say resulting from the action of enzymes such as plant or animal lipoxygenases, cyclo-oxygenases or microsomal cytochrome P-450 oxygenases.

Finally, it may result from the coupling of enzymatic and non-enzymatic reactions. This is, for example, the case for lipid oxidations associated with the monovalent reduction of certain xenobiotics, in the presence of oxygen and of enzymatic reducing systems.

Decomposition of the lipid peroxides results in the formation of very many organic by-products.

This decomposition may be of enzymatic origin (for example the action of peroxidases and/or of thromboxane synthetase) or non-enzymatic origin (thermal, photochemical, reducing, or catalysed by transition metal complexes).

Among the main organic by-products of the decomposition of lipid peroxides there may be mentioned certain alcohols, conjugated dienes, conjugated trienes, volatile hydrocarbons such as ethane, pentane or ethylene, certain saturated, unsaturated and/or hydroxylated aldehydes or ketones, certain saturated or unsaturated epoxides, Schiff's bases arising from the reaction of the abovementioned aldehydes with the amino groups of molecules present in the medium and the associations of certain abovementioned compounds with polyfunctional molecular stuctures.

The expression "lipid peroxidation" thus defined applies exclusively to the routes of formation and degradation of the free or esterified PUFA peroxides.

The pronounced propensity to oxidation of the PUFA's is due to the systematic presence in these compounds of the cis,cis-1,4-pentadiene moiety which makes possible a stabilizing delocalization of the radical intermediates initially produced by homolytic scission of a methylene C—H bond, as shown the scheme which follows.

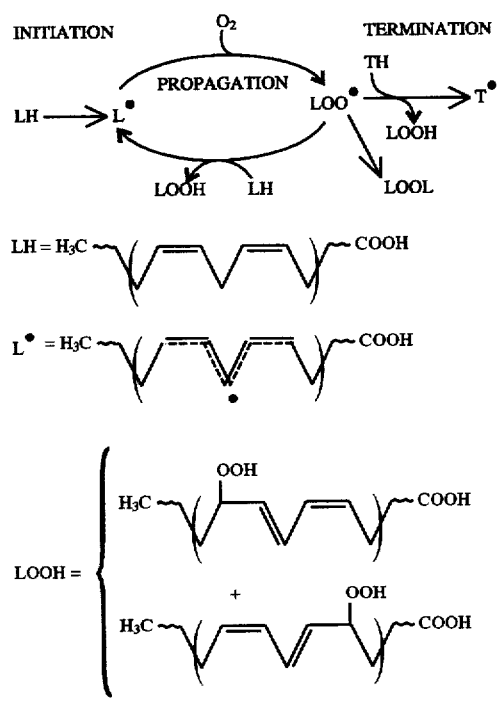

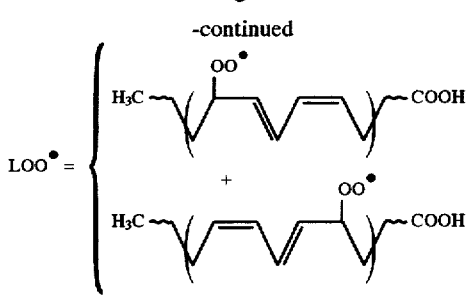

$$LOO^\bullet = \left\{ \begin{array}{c} H_3C \diagup\!\!\!\diagdown\!\!\!\diagup\!\!\!\diagdown\!\!\!\diagup\!\!\!\diagdown COOH \\ + \\ H_3C \diagup\!\!\!\diagdown\!\!\!\diagup\!\!\!\diagdown\!\!\!\diagup\!\!\!\diagdown COOH \end{array} \right.$$

In biological media the most important PUFA's are those which are derived from linoleic acid and from α-linolenic acid, that is to say those which belong to the classes known as "n-6" and "n-3" respectively.

Any measurement of the lipid peroxidation index (indices) must therefore also be as specific as possible for the peroxidation products or by-products of the abovementioned PUFA's.

A large number of methods for measurement of lipid peroxidation have been described in the past. These may be divided into five main classes:

1. Direct or indirect spectrophotometric methods.
2. Spectrofluorimetric methods.
3. Electrochemical methods.
4. Chemiluminescent methods.
5. Chromatographic methods.

The methods belonging to the classes 2 to 5 have recently been described (references 1 and 2). They pose problems of specificity or instrumental complexity which preclude their routine use by non-specialized laboratories.

The known direct spectrophotometric methods of class 1, to which the present invention belongs, are summarized below.

The standard method for the "conjugated dienes" is based on a measurement of the absorbance that 233 nm, which makes it possible to quantify the bis-allylic (trans-dienic) structures of the hydroperoxides and alcohols of PUFA, with higher sensitivity.

In the majority of biological samples, the presence of other dienic structures and the very intense absorption of carbonyl groups and of monoalkenes unfortunately produce serious interferences which can only be eliminated by differential spectroscopy procedures, which are generally incompatible with an assay on a biological sample of unknown composition.

Colorimetric assay of malonic dialdehyde (1,3-propanedial or MDA) gives the most commonly used lipid peroxidation index (reference 2).

MDA is both an enzymatic metabolite of arachidonic acid and a secondary product of peroxidation of PUFA's (reference 3).

The main route for enzymatic production of MDA is that of thromboxane synthetase (reference 4) which converts prostaglandin $PGH_2$ (endoperoxide) to thromboxane $A_2$, L-12-hydroxy-5,8,11-heptatrienoate and MDA (in the respective proportions ⅓, ⅓, ⅓).

MDA of non-enzymatic origin is formed by radical decomposition of mono- or bicyclic endoperoxides derived from a bis-allylic peroxyl radical.

The chemical and biochemical properties of MDA have been the subject of a detailed review (reference 5).

MDA is a volatile compound which is totally enolized, in monoenol-monoaldehyde form, in aqueous or organic solution. It displays both nucleophilic (enolate) and electrophilic (aldehyde) properties, which explains its tendency to self-polymerize to give a mixture of more or less reversible oligomeric adducts.

When it is heated at acidic pH, MDA reacts with a certain number of nucleophilic compounds to give various condensation products.

Quantification or assay methods have been proposed for some of the MDA condensation products, but none is totally satisfactory.

Pyrazolebenzothiazole derived from 2-hydrazinobenzothiazole, or 1-methylpyrazole derived from methylhydrazine, may be quantified by gas phase chromatography (methods of class 5) due to their high volatility.

N-Methylpyrrole (reference 6) gives a chromophoric adduct which is characteristic of MDA. However, its half-life is too short for colorimetric measurements to be possible on large series of samples.

2-Methylindole also leads to a chromophoric adduct with MDA, but the molar extinction coefficient is much too low (em #32,000 l.mole$^{-1}$.cm$^{-1}$) to make an assay of MDA at physiological concentrations (0.5–5 µmolar) possible (reference 7).

In practice, thiobarbituric acid (TBA) is currently almost exclusively used to assay MDA by colorimetry, on account of the high stability and molar extinction coefficient at 530–535 nm of the chromophoric condensation product which is formed by addition of two molecules of TBA to one molecule of MDA. In addition, as this product is fluorescent, it may also be assayed by spectrofluorimetry.

All the assay procedures for MDA and/or the lipid peroxidation products reacting with TBA, hereinafter referred to as "TBARS" (TBA-Reactive Substances) require an acidic pH (<3.8) and prolonged heating (80°–95° C., 20–60 min). The acidification and heating of the samples generally leads to a cloudy suspension which must be clarified before the measurement, for example by extraction with n-butanol.

Variants of the test for TBA are very numerous, emphasizing that this approach poses problems, especially regarding its reliability (reference 8). In fact, the test for TBA poses two main problems, namely:

the temperature and pH conditions required bring about secondary reactions leading to artefactual products which react with the TBA, thus distorting the assay; and TBA is not a reagent which is specific for MDA.

A first source of interferences is due to the presence of aldehydes of lipid origin, but distinct from the MDA. A certain number of monoaldehydes react with TBA under the standard conditions of the test to give products which interfere with the absorption of the MDA:TBA (1:2) adduct (reference 9).

The yield for formation of certain pigments is uncertain, because it depends on the respective concentrations of aldehydes and of certain intermediate adducts simultaneously present in the sample. Some of these chemical mechanisms have been discussed (reference 10).

The coloured products due to the presence of monoaldehydes of lipid origin generally have one or more absorption bands between 450 nm and 500 nm which are broad and overlap with that of the MDA:TBA (1:2) adduct. They may multiply the absorption at 530–535 nm by a considerable factor because, on an extract of oxidized lipids, the sum of the amounts of monoaldehydes produced may exceed the MDA production (reference 5).

The second source of interferences is due to the formation of MDA or TBARS from non-lipid compounds. Deoxyribose and its nucleoside derivatives (reference 11), as well as pyrimidine and 2-aminopyrimidine, behave like authentic MDA under the test conditions (reference 8).

Moreover, sugars such as sucrose and glucose have a powerful synergic effect on the formation of TBARS in the presence of various peroxides or aldehydes such as acetaldehyde (reference 12), whereas these molecules do not form TBARS when they are present separately.

Sialic acid (N-acetylneuraminic acid) produces an adduct absorbing intensely at around 550 nm (reference Bilirubin, biliverdin and hemolysed serum also produce a "contaminating" absorption.

The test for TBA thus poses specificity problems due to:
- the formation of TBARS of lipid origin, adding to the MDA,
- the existence of reaction interferences (formation of MDA or TBARS) due to contaminants of non-lipid origin which are active under the test conditions.

The overlapping of the absorption or fluorescence spectra of the contaminating adducts with the spectrum of the MDA:TBA (1:2) adduct does not make it possible to improve the specificity of the measurements by using multiple wavelengths.

Chromatographic separation of the MDA adduct also does not make it possible to eliminate the problems of artefactual formation of authentic MDA under the test conditions for TBA.

These difficulties have led a certain number of laboratories to develop chromatographic assay methods for MDA as well as for other aldehydes (reference 1).

These procedures are long and complicated. They are thus difficult to use routinely on large series of samples, but their development has made it possible to point out the importance of the production of MDA and other aldehydes in lipid peroxidation phenomena.

Esterbauer and his colleagues have thus shown that the production of 4-hydroxynonenal (4-HNE) was characteristic of lipid peroxidation phenomena (reference 13).

The oxidation of "n-6" PUFA's is at the origin of this production of 4-HNE, for which the yield is maximal with arachidonic acid 20:4 (n-6).

A related compound, 4-hydroxyhexenal, is produced from "n-3" PUFA's.

To summarize, it is known that MDA and/or other enaldehydes in a medium, in particular a biological medium, constitute lipid peroxidation indices, but methods which are reliable and easy to implement have not hitherto been available to assay them.

The aims of the present invention are thus in particular:
- to make available new reagents reacting with the 4-hydroxy-2-enaldehydes, and especially MDA;
- to make available a colorimetric assay for the enaldehydes and for their acid-labile derivatives such as acetals, thioacetals, imines, enol ethers or enol thioethers as lipid peroxidation indices, by quantitative production of condensation products which are stable and which bear a similar sole chromophoric structure for which the maximum absorption wavelength is greater than or equal to 570 nm, it being understood that the term "enaldehyde" applies to the group comprising 4-hydroxy-2-enaldehydes and MDA. The 4-hydroxy-2-enaldehydes are for instance 4-hydroxynonenal, 4-hydroxyhexenal, 4-hydroxydecenal and 4-hydroxydodecanal, as well as MDA;
- to make possible a colorimetric assay which is specific for MDA at the same absorption wavelength as that for the assay of the 4-hydroxy-2-enaldehydes.

These aims are achieved by virtue of the invention, which uses novel chemical reagents and which exploits the chromogenic properties of the addition products of these reagents towards enaldehydes.

These reagents are characterized, in particular, by the presence of an indole ring system which is not substituted in position 3 and by their solubility in polar protic solvents such as water, methyl and ethyl alcohols and acetonitrile among others. The chromophore generated by addition of these reagents to the enaldehydes displays a maximum absorption wavelength which is always greater than or equal to 570 nm.

The invention provides a simple and rapid process implementing these reagents, which process makes it possible to assay enaldehydes and their acid-labile derivatives such as acetals, thioacetals, imines, enol ethers or enol thioethers by colorimetry as lipid peroxidation indices, by quantitative production of condensation products which are stable and which bear a similar sole chromophoric structure, under temperature conditions which are much milder than in the TBA method, considerably limiting the potential artefacts due to heating at high temperature for a long period. This process is thus well suited to a routine assay on large series of samples.

More precisely, according to one of its aspects, the subject of the invention is a process for colorimetric assay of total enaldehydes or of malonic dialdehyde alone, as lipid peroxidation indices in a medium, especially a biological medium, characterized in that it essentially comprises:

a) addition to the said medium of a reagent chosen from compounds of general formula I below and their optional addition salts with organic or inorganic bases, or with organic or inorganic acids:

in which formula:

A and C, which may be identical or different, each represent H,

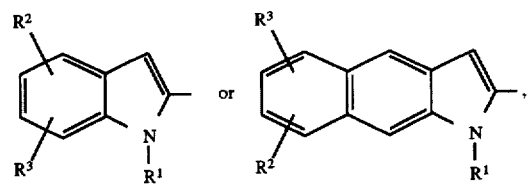

it being understood that

A and C cannot simultaneously represent H, with:

$R^1$=H; alkyl; aralkyl; aralkyl substituted on the aryl ring; alkyl sulfonate, $Y^+$; alkyl phosphonate, $Y^+$; or alkyl carboxylate, $Y^+$;

$R^2$=H; —$OR^4$; F; Cl; Br; I; —$NO_2$; —$SO_3^-Y^+$; —CN; —$COOR^4$; or —$CONR^5R^6$;

$R^3$=H; —$OR^4$; —$NR^5R^6$; —$SR^4$; F; Cl; Br; I; —$NO_2$; —$SO_3^-Y^+$; —CN; —$COR^5$; —$COOR^4$; or —$CONR^5R^6$;

$R^4$=H; alkyl; aralkyl; or aralkyl substituted on the aryl ring;

$R^5$=H; alkyl; aralkyl; or aralkyl substituted on the aryl ring;

$R^6$=H; aryl, aralkyl; or aralkyl substituted on the aryl ring;

$Y^+$=cation of an organic or inorganic base;

B =

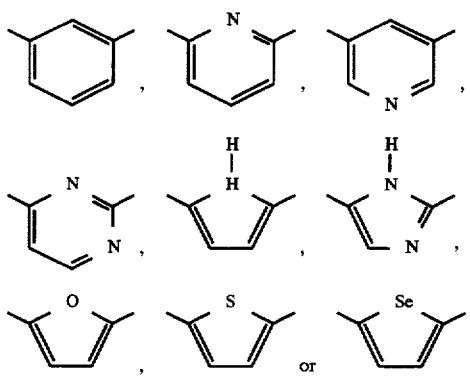

it being understood that:
  alkyl represents a linear or branched group comprising 1 to 6 C;
  aralkyl substituted on the aryl ring means that the latter is substituted with one or more groups, which may be identical or different, chosen from (1 to 6 C) alkyl, (1 to 6 C) alkoxy, hydroxy, amino and carboxyl;
b) acidification of the medium which has been thus added to, either by an acid chosen from-the group consisting of strong carboxylic acids, strong sulfonic acids and perchloric acid, or by hydrochloric acid, hydrobromic acid or sulfuric acid;
c) incubation of the medium thus acidified at a temperature between 25° and 60° C., for a sufficient period to obtain a stable coloration due to the formation of a chromophoric addition product of the reagent with all the enaldehydes present in the medium or with malonic dialdehyde alone, according to the nature of the acid used;
d) measurement of the absorbance of the colored medium at the absorption wavelength which is specific for the chromophoric addition product of the reagent used, and its utilization for determining the total enaldehyde concentration, or the concentration of malonic dialdehyde alone, as appropriate.

When, in the chosen compound of general formula I, $R^4$=H, its addition salt with an inorganic or organic base may be used, which base may be chosen, for example, from sodium hydroxide, potassium hydroxide, metal alkali carbonates, alkaline-earth metal carbonates, triethylamine and arginine.

When, in the chosen compound of general formula I, $R^5$ and/or $R^6$=H, its addition salt with an inorganic or organic acid may be used, which acid may be chosen, for example, from hydrochloric, hydrobromic, hydroiodic, sulfuric, tartaric, methanesulfonic and trifluoromethanesulfonic acids.

Incubation leading to the formation of the chromophore must take place in acidic medium.

The incubation period essentially depends upon the temperature used. It generally does not exceed 1 hour and it is most often lower than this.

According to the invention, it has been found that the reagents of general formula I react, in the presence of some acids, with all the enaldehydes resulting from the lipid peroxidation process as defined above or with MDA alone, to lead to a chromophoric addition product which is stable for a long period, for which the maximum absorption wavelength is in all cases greater than or equal to 570 nm and depends upon the nature of the reagent of formula I.

More precisely, in the presence of a strong carboxylic acid, a strong sulfonic acid or perchloric acid, the reagents of general formula I react with all the enaldehydes present in the medium, whereas in the presence of hydrochloric acid, hydrobromic acid or sulfuric acid, they essentially only react with MDA, to form the chromophoric compound characteristic of the reagent used.

Every acid is advantageously separately packaged. It must be of ultra-pure quality and advantageously stored in pure form or as a mother solution diluted in deionized water, at a concentration not lower than 5 moles/liter.

In the process, it is advantageous that the final concentration of the acid in the final reaction medium be generally ranging between 0.5 and 2.5 moles/liter.

With regard to the reactant of general formula (I), it may advantageously be taken in the form of a mother solution in a compatible organic solvent such as for instance an organic solvent miscible with water such as notably acetonitrile, DMSO, THF, methanol, ethanol or isopropanol or in neutral or acidified water or in a buffer.

The concentration of the reactant in the mother solution is generally advantageously ranging between 5 and 40 mmoles/liter, in function of its solubility in the solvent used.

This reactant will in most cases be diluted at the time of use to get a final concentration in the final reactant medium advantageously ranging between 3 and 25 mmoles/liter.

The invention therefore makes it possible to assay not only all the enaldehydes present in the medium tested, but also specifically to assay MDA in the presence of 4-hydroxy-2-enaldehydes in a sample, especially a biological sample.

The process according to the invention therefore makes it possible to measure the overall amount of enaldehydes on a first sampling, followed by that of MDA on a second sampling, or the contrary. The very mild operating conditions of this new process, by making it possible to eliminate most of the very numerous artefacts linked with the TBA method, make this a particularly reliable and reproducible method.

The reagents of general formula I collectively lead to the formation of a chromophore for which the common structure is of the type:

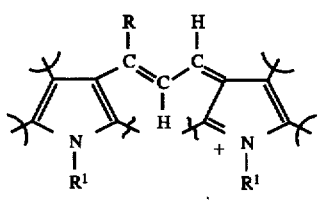

In the case of MDA (R=H), formation of the chromophore does not require any oxidation step, whereas in the case of the 4-hydroxy-2-enaldehydes, an oxidation is necessary and the reaction medium cannot therefore be degassed in ambient oxygen.

Trifluoroacetic acid may be mentioned as a strong carboxylic acid which may be used.

Methanesulfonic acid and trifluoromethanesulfonic acid may be mentioned as strong sulfonic acids which may be used.

It has, however, been found that, depending on the degree of purity of the acids and reagents used, the yield for formation of the chromophore may vary significantly when enaldehydes other than MDA are involved in the reaction.

According to another aspect of the invention, it has been found that addition of a metal salt such as, for example, a 5 micromolar ferric iron salt in the final reaction medium made it possible to obtain a yield which was reproducible and maximal for formation of the chromophore with all the enaldehydes tested.

The new assay method according to the invention constitutes a new tool for biological research in general as well as in clinical chemistry, in particular for the development of assay kits which may be used in research or in quality control, or alternatively in the field of medical diagnostics.

The method may thus be used to evaluate the degree of spoilage of food products as well as that of nutritive solutions used via the enteral or parenteral route.

In the field of medical diagnostics, the method may be used to confirm a pathological state such as pre-eclampsia in pregnant women and hypertension, unstable angina and silent myocardial ischaemia.

It may also be used to confirm the effectiveness of an arterial or angioplastic thrombolysis intervention.

It may finally provide a therapeutic efficiency index during the treatment of states of shock (septic or traumatic), certain acute intoxications, diabetes, AIDS, certain malnutrition states, and genetic diseases of an excess of iron.

It may finally also be used in the post-operative follow-up of organ transplants and/or of extra-corporal circulation procedures.

The samples targeted are especially biological samples such as whole or deproteinized blood plasma, red corpuscle lysates, cerebro-spinal fluid, plasma lipoproteins obtained by selective precipitation or solid tissue homogenates.

The sample to be assayed may be essentially liquid such as, for example, an extract, a solution or a dispersion of a material, especially a biological material, in an aqueous medium optionally buffered or in a water-miscible organic solvent.

It may, for example, be a centrifugation pellet of a biological sample dispersed in an optionally buffered aqueous medium or an organic medium.

The liquid samples may be aqueous solutions which are deproteinized by precipitation using acids such as, for example, metaphosphoric acid, trichloroacetic acid or phosphotungstic acid.

These samples may contain a neutral or cationic detergent (especially in an amount of 0 to 2 g per 100 ml), for example Lubrol® (condensate of polyethylene oxide) or a tetraalkylammonium salt.

In any case, the proportion by volume of the sample in the final reaction medium (after addition of the acid) must be compatible with obtaining a single liquid phase in this medium.

Incubation of the sample with the reagent of formula I to form the chromogenic addition compound must be carried out at a temperature not exceeding 60° C., in order to avoid secondary reactions leading to artefactual products, the presence of which would distort the assay.

Depending on the reagent of formula I used, the incubation time for the reaction medium at the chosen temperature must be set so as to achieve a stable plateau corresponding to a maximum production yield for the chromophore measured. The incubation time is generally less than or equal to 60 minutes.

For assay of the total enaldehydes, the final reaction medium must not be degassed. It may be done when MDA is assayed alone, in a specific manner. However, it is generally preferable that the final reaction medium consist of solutions and solvents which have not been degassed beforehand in ambient oxygen.

Spectrophotometric measurement of the absorbance of the chromophore produced by reaction of the enaldehydes or of MDA alone with a chromogenic reagent of general formula I and in the presence of a strong acid must be carried out at a wavelength which is set and in the region ($\pm 5$ nm) of the maximum absorption wavelength ($\geq 570$ nm) of the chromophore which is specific for the reagent used.

According to an advantageous embodiment, the total enaldehyde concentration or the concentration of malonic dialdehyde alone, depending on the case, is determined by means of a calibration curve.

This calibration curve may be produced from an aqueous or organic solution of known concentration of any one of the enaldehydes or of their acid-labile precursors as defined above. The solvent must be chosen so as to avoid any polymerization of the aldehyde used or any hydrolysis of the precursor used, for the period of utilization of the solution.

A standard solution containing an enaldehyde which is likely to be found in the medium to be assayed, for example MDA or 4-hydroxynonenal (4-HNE) or any enaldehyde usually formed in the course of the lipid peroxidation process, is advantageously used.

The standard solution used must have a concentration such that it can be diluted in order to obtain several points for the calibration curve.

In order to obtain a calibration curve, working under the prearranged assay conditions (acidification and incubation), the difference between the absorbance A for a given concentration and the absorbance $A_0$ for a control not containing aldehyde is plotted as a function of the known concentration of enaldehyde, these absorbances being read at the maximum absorption wavelength characteristic of the addition product between the enaldehydes and the reagent used.

A straight line is thus obtained for which the slope is equal to the apparent molar extinction coefficient E of the addition compound measured.

Various tests in particular with MDA, 4-hydroxynonehal and 4-hydroxyhexenal have shown that regardless of the enaldehyde used, the slope of the straight line is virtually the same for a same given reagent of formula I. It is thus possible to use, in order to establish the calibration curve, any one of the enaldehydes which is likely to be present in the medium to be assayed.

MDA or 4-hydroxynonenal, which are easy to gain access to, are advantageously used.

In the particular case of the assay of MDA alone, the calibration curve is preferably established under the conditions particular to this assay (acidification by hydrochloric acid or hydrobromic acid), by using MDA which, as will be seen in greater detail in the experimental section which follows, is virtually the only enaldehyde which reacts under these conditions.

The concentration of enaldehydes sought may be determined from the measurement of the absorbance A of the sample and the measurement of the absorbance $A_0$ made on a control not containing aldehyde and from the molar extinction coefficient E which corresponds to the slope of the calibration straight line.

This thus gives:

[enaldehyde concentration]$=(A-A_0)\times K/E$.

In this equation:

the enaldehyde concentration is expressed in moles.$l^{-1}$;

A and $A_0$ are read with an optical path length of 1 cm and are expressed in $cm^{-1}$;

K is the dilution factor; and

E is expressed in $l.moles^{-1}.cm^{-1}$.

The enaldehyde concentration may also be deduced directly from the calibration curve using the measurement A, by using the difference $A-A_0$.

According to another of its aspects, a subject of the invention is a requisite or kit for the implementation of the assay process described above, characterized in that it essentially contains a reagent corresponding to the general formula I defined above.

This reagent is advantageously present as a mother solution in a compatible solvent such as, for example, a water-miscible organic solvent such as especially acetonitrile, DMSO, THF, methanol, ethanol or isopropanol, or alternatively in neutral or acidified water or in a buffer.

The concentration of the reagent in its mother solution is in general between 5 and 40 mmoles/l, depending on its solubility in the solvent used.

This reagent will most often be diluted at the time of use in order advantageously to obtain a final concentration in the final reaction medium between 3 and 25 mmoles/l.

According to a preferred embodiment, the requisite or kit according to the invention comprises in addition at least one strong acid chosen from the group consisting of strong organic acids such as trifluoroacetic acid, strong sulfonic acids such as methanesulfonic acid or trifluoromethanesulfonic acid, perchloric acid, sulfuric acid, hydrochloric acid and hydrobromic acid.

Each acid is packaged separately. It must be of ultra-pure quality and is advantageously stored in pure form or in the form of a mother solution diluted in deionized water, to a concentration not lower than 5 moles/l.

The final concentration of the acid in the final reaction medium will in general be between 0.5 and 2.5 moles/l.

According to another preferred embodiment, the requisite or kit according to the invention comprises in addition, as reference or standard sample, at least one lipid peroxidation index enaldehyde or one acid-labile precursor for such an enaldehyde, in aqueous or organic solution, at a known concentration.

Figure 1:
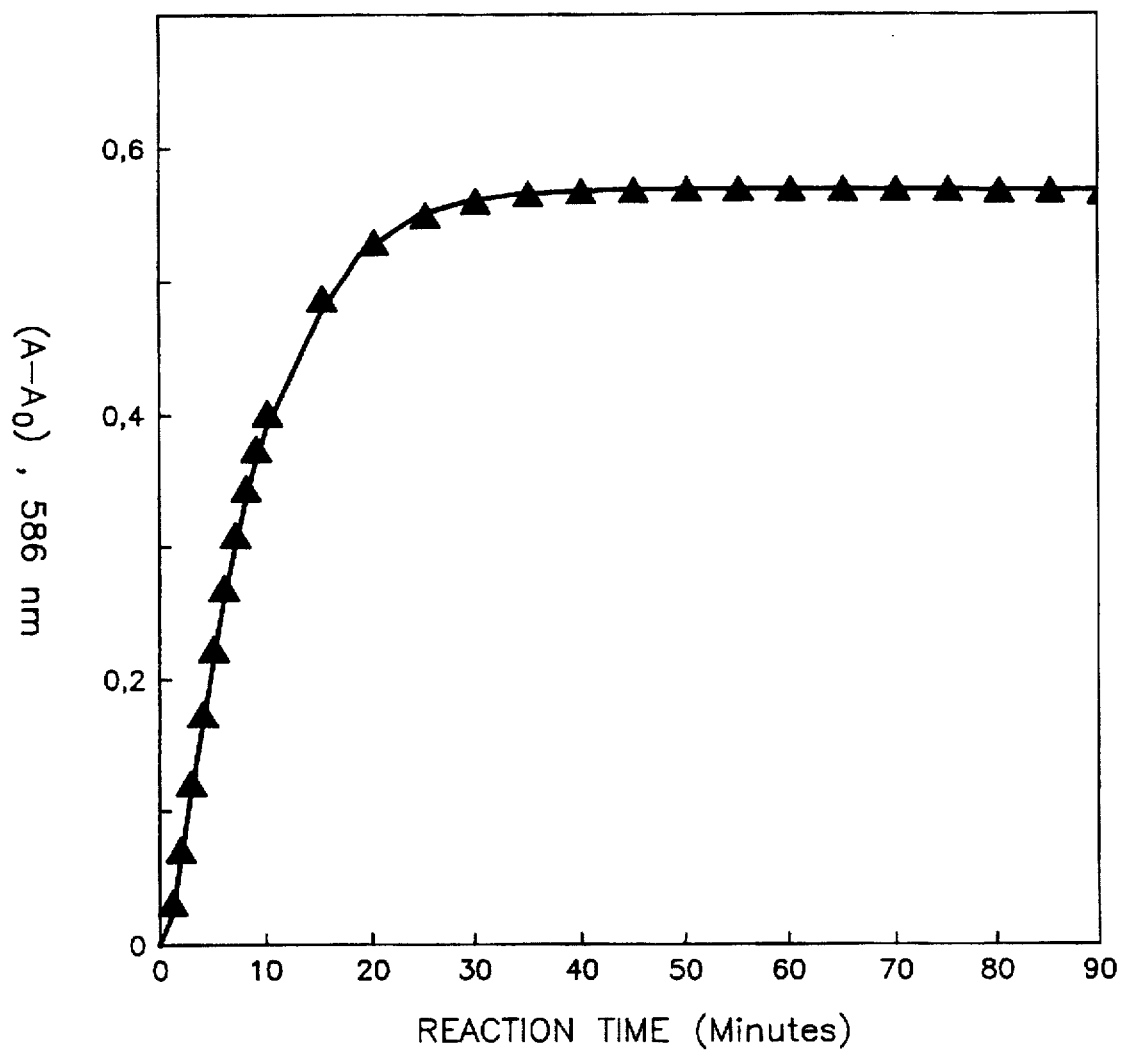
FIG. 1 annexed shows the kinetics for formation of the adduct of tetramethoxypropanne (IMP) with 1-methyl-2-phenylindole (MPI), during incubation at 45° C. with methanesulfonic acid (reagent R2) at a concentration of 15%.

The compounds of general formula I may be prepared according to the general procedures 1 to 3 described below.

General procedure 1: Fischer method

This general procedure for the preparation of the compounds of general formula I is based on the methods described in the literature (reference 14).

It essentially comprises three steps from an arylhydrazine hydrochloride which is substituted or otherwise, as summarized in the following scheme I:

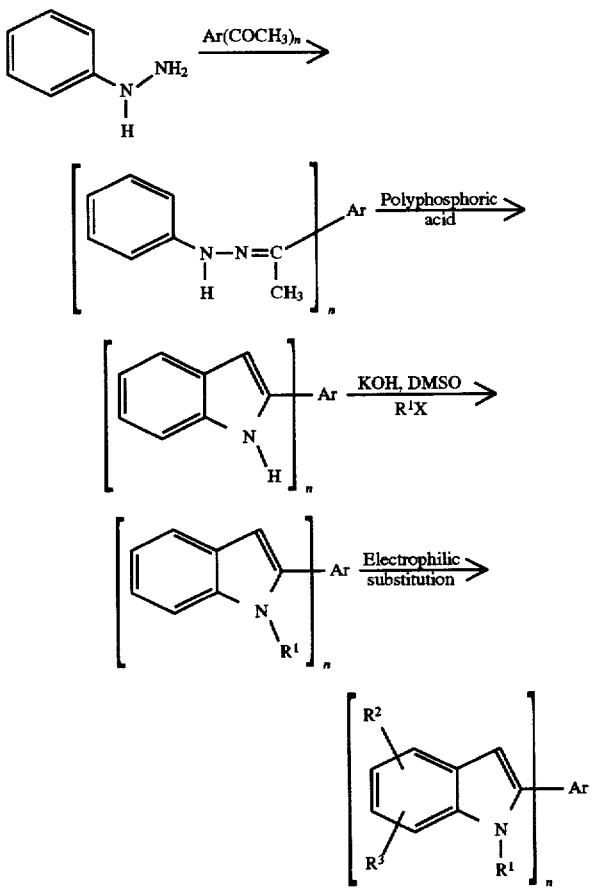

To a solution of commercial arylhydrazine hydrochloride at reflux is added a solution of the corresponding acetylated aromatic derivative, which is itself commercial or prepared according to one of the known methods (reference 15). The reflux is maintained for 15–90 minutes. After cooling, the desired product precipitates or crystallizes. In some cases, a purification by liquid chromatography on a silica column turns out to be necessary.

The cyclization step is carried out using polyphosphoric acid according to the standard procedure. The desired product is obtained after purification by liquid chromatography on an alumina column and is recrystallized.

Alkylation of the indole derivative requires a first phase of generation of the anion by reaction with powdered potassium hydroxide in dimethyl sulfoxide at room temperature for several hours; the alkylating agent such as, for example, methyl sulfate is subsequently added. After the usual treatment, the desired product is obtained after purification by liquid chromatography on a silica column and is recrystallized.

Examples 1 to 7 illustrate this general procedure 1.

General procedure 2: according to reference 16

This procedure essentially contains three steps from a compound of 2-ethynylaniline type, which is substituted or otherwise, as summarized in the following scheme II:

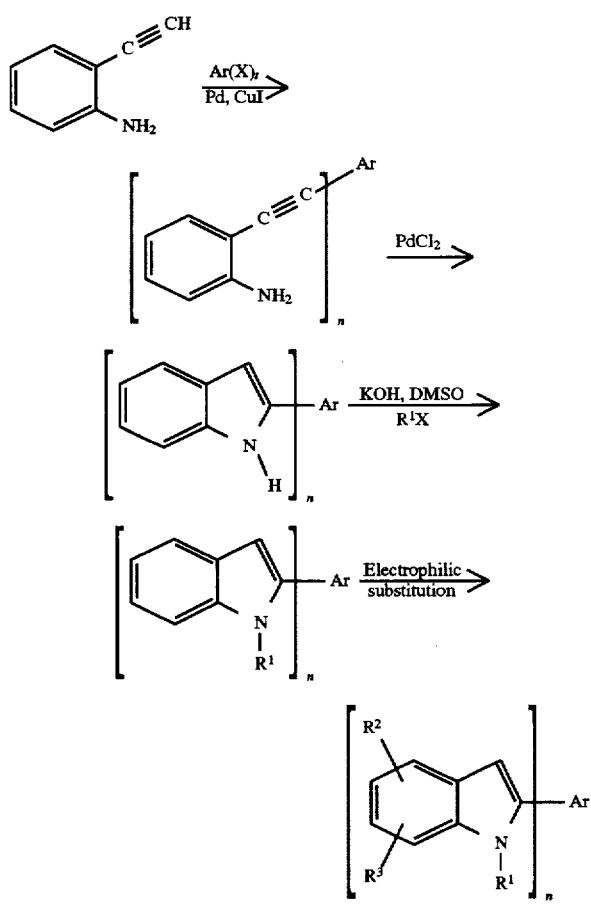

n = 1 or 2.

The compound of 2-ethynylaniline type is subjected to the action of an aryl halide or trifluoromethanesulfonate in the presence of palladium zero (Pd⁰) and cuprous iodide (CuI) at room temperature for 1 to 6 hours. The corresponding substituted aryl derivative is obtained after the usual treatment and purification by liquid chromatography on a silica or alumina column.

The cyclization step is carried out using a catalytic amount of palladium chloride (PdCl₂) by heating the above derivative in refluxing acetonitrile for 2–30 hours. The desired product is obtained after liquid chromatography on a silica or alumina column, or after recrystallization.

Alkylation is carried out in the same way as for the procedure 1.

Examples 8 to 11 illustrate this general procedure 2.

General procedure 3: according to reference 17

This procedure essentially contains four steps from a compound of 2-haloaniline or 3-amino-2-halonaphthalene type which is substituted or otherwise, as summarized in the following scheme III:

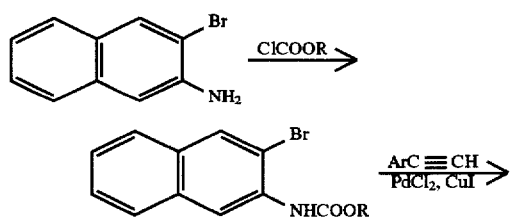

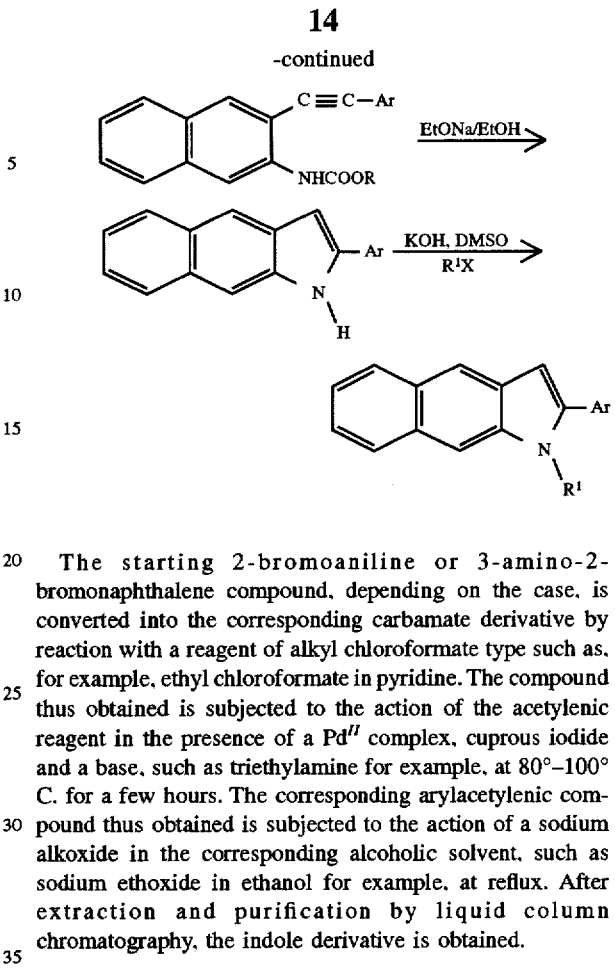

The starting 2-bromoaniline or 3-amino-2-bromonaphthalene compound, depending on the case, is converted into the corresponding carbamate derivative by reaction with a reagent of alkyl chloroformate type such as, for example, ethyl chloroformate in pyridine. The compound thus obtained is subjected to the action of the acetylenic reagent in the presence of a Pd$^{II}$ complex, cuprous iodide and a base, such as triethylamine for example, at 80°–100° C. for a few hours. The corresponding arylacetylenic compound thus obtained is subjected to the action of a sodium alkoxide in the corresponding alcoholic solvent, such as sodium ethoxide in ethanol for example, at reflux. After extraction and purification by liquid column chromatography, the indole derivative is obtained.

The alkylation is carried out in the same way as for the procedure 1.

Example 12 illustrates this general procedure 3.

The compounds of general formula I in which:

A, B and C, as well as $R^1$ to $R^6$, are defined as above, it being understood that when A or C represents H and the other substituent C or A represents

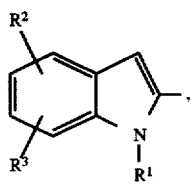

$R^2$ and $R^3$ are other than H; OR$^4$ when A or C represent H, the other substituent C or A represents

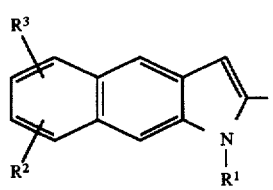

and B represents

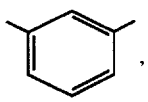, $R^1$, $R^2$, $R^3$ do not simultaneously represent H, are new and constitute one of the subjects of the present invention.

The invention will be explained in greater detail with the aid of the non-limiting examples given in the experimental section which follows.

EXPERIMENTAL SECTION

I. Preparation of the compounds used according to the invention:

All the reactions are carried out under an inert atmosphere of nitrogen, unless otherwise indicated.

The mass spectra (MS) are recorded on a Nermag R10–10B apparatus. The mode of ionization used is either electron impact (EI) at 70 electron-volts, or chemical ionization (CI) in ammonia, or fast atom bombardment (FAB) on a glycerol matrix.

$^1$H and $^{13}$C NMR spectra are recorded on a Varian Gemini-200 apparatus. The chemical shifts are expressed in ppm relative to tetramethylsilane. The multiplicities are expressed as follows: "s" for singlet, "bs" for broad singlet, "d" for doublet, "t" for triplet and "m" for multiplet.

Melting points (m.p. °C.) are recorded on a Gallenkamp apparatus and are given uncorrected.

Purifications by liquid column chromatography are carried out either with Merck® Si 60 silica, or with Merck® neutral alumina of activity II–III.

A. Examples using the procedure 1:

EXAMPLE 1

Preparation of 1,1'-dimethyl-2,2'-(m-phenylene)di-indole:

1,3-Diacetylbenzene bis(phenylhydrazone)

1,3-Diacetylbenzene (6.48 g; 40 mmol) dissolved in 20 ml of ethanol is added to a solution of phenylhydrazine hydrochloride (12.72 g; 88 mmol) and sodium acetate (19.68 g; 240 mmol) in 80 ml of water at reflux. The reaction mixture is maintained under these conditions for 30 minutes after the end of the addition. After cooling to room temperature, it is stirred for 3 hours at 0° C. The suspension thus obtained is filtered. The precipitate is washed with 2×50 ml of water and then dried under vacuum. The desired product is obtained after recrystallization (95% ethanol).

Yield: 13.41 g; 98%.
Physical characteristics:
$^1$H NMR (DMSO-$d_6$): 2.27 ppm (s, 6H); 6.78 ppm (m, 2H); 7.20–7.32 ppm (m, 8H); 7.40 ppm (t, 1H, J=8 Hz); 7.68 ppm (d, 2H, J=8 Hz); 8.29 ppm (bs, 1H); 9.31 ppm (s, 2H).

2,2'-(m-Phenylene)di-indole

The product obtained above is dissolved at 90° C. in 100 ml of polyphosphoric acid. The mixture thus obtained is heated for 3 h at 120°–130° C. The reaction mixture is then poured into 800 ml of ice-water; complete dissolution of the acid requires approximately 1.5 h. A precipitate appears in the course of this step. The suspension obtained is filtered and then washed with 2×200 ml of water. The residue is redissolved in 400 ml of ethyl acetate and washed with saturated sodium chloride solution until neutral. The organic phase is dried over magnesium sulfate. The solvent is evaporated under reduced pressure. The desired product is obtained after purification by liquid chromatography on an alumina column (elution gradient: hexane/ethyl acetate 6:1 to 4:1).

Yield: 3.85 g; 32%.
Physical characteristics:
Melting point: 282° C. decomp.
$^1$H NMR (DMSO-$d_6$): 6.98–7.18 ppm (m, 6H); 7.44 ppm (d, 2H, J=8 Hz); 7.55 ppm (t, 1H, J=7 Hz); 7.58 ppm (d, 2H, J=8 Hz); 7.80 ppm (dd, 2H, J=1.5–7 Hz); 8.39 ppm (t, 1H, J=1.5 Hz).

1,1'-Dimethyl-2,2'-(m-phenylene)di-indole

To a solution of the 2,2'-(m-phenylene)di-indole obtained above (3.85 g; 12.5 mmol) in 30 ml of dimethyl sulfoxide is added powdered potassium hydroxide (5.6 g; 100 mmol). The reaction mixture is stirred for 64 h at room temperature. Methyl sulfate (15.75 g; 125 mmol) is then added. After 15 minutes, 100 ml of water is added to the reaction mixture. The product is extracted with 300 ml of ethyl acetate. The organic phase is washed with 2×100 ml of saturated sodium chloride solution and then dried over magnesium sulfate. The desired product is obtained after recrystallization (hexane/ethyl acetate 1:1).

Yield: 3.33 g; 81%.
Physical characteristics:
Melting point: 150° C.
$^1$H NMR (DMSO-$d_6$): 3.83 ppm (s, 6H); 6.68 ppm (s, 2H); 7.08 ppm (m, 2H); 7.21 ppm (m, 2H); 7.52 ppm (d, 2H, J=8 Hz); 7.59 ppm (d, 2H, J=7.5 Hz); 7.67 ppm (s, 3H); 7.79 ppm (s, 1H).
$^{13}$C NMR (DMSO-$d_6$): 31.25 ppm; 101.84 ppm; 110.47 ppm; 119.95 ppm; 120.45 ppm; 121.90 ppm; 127.69 ppm; 127.71 ppm; 128.79 ppm; 129.51 ppm; 132.95 ppm; 138.56 ppm; 140.83 ppm.
MS (EI, 70 eV): 336 (100, M$^+$); 320 (12); 204 (10); 168 (30).

EXAMPLE 2

Preparation of 5-Fluoro-1-methyl-2-(2'-thienyl) indole

2-Acetylthiophene 4-fluorophenylhydrazone

This compound is prepared from commercial 4-fluorophenylhydrazine hydrochloride (Aldrich) and from commercial 2-acetylthiophene (Aldrich), according to the procedure 1.

Yield: 71%.
Physical characteristics:
$^1$H NMR (DMSO-$d_6$): 2.25 ppm (s, 3H); 6.98–7.20 ppm (m, 5H); 7.23 ppm (d, 1H, J=3.0 Hz); 7.40 ppm (d, 1H, J=5.0 Hz); 9.30 ppm (bs, 1Hh).

5-Fluoro-2-(2'-thienyl)indole

This compound is prepared from the 2-acetylthiophene 4-fluorophenylhydrazone obtained above, according to the procedure 1.

Yield: 46%.
Physical characteristics:
$^1$H NMR (DMSO-$d_6$): 6.65 ppm (s, 1H); 6.93 ppm (td, 1H, J=2.5–9.0–9.0 Hz); 7.15 ppm (dd, 1H, J=3.5–5.0 Hz));

7.25 ppm (dd, 1H, J=2.5–10.0 Hz)); 7.34 ppm (dd, 1H, J=4.5–9.0 Hz); 7.50–7.58 ppm (m, 2H); 11.66 ppm (bs, 1H).

5-Fluoro-1-methyl-2-(2'-thienyl)indole

This compound is prepared from the 5-fluoro-2-(2'-thienyl)indole obtained above, according to the procedure 1.

Yield: 74%.
Physical characteristics:

$^1$H NMR (DMSO-d$_6$): 3.85 ppm (s, 3H); 6.65 ppm (s, 1H); 7.15 ppm (td, 1H, J=2.5–9.0–9.0 Hz)); 7.23 ppm (dd, 1H, J=3.5–5.0 Hz); 7.35 ppm (dd, 1H, J=2.5–10.0 Hz); 7.43 ppm (d, 1H, J=3.5 Hz); 7.53 ppm (dd, 1H, J=4.5–9.0 Hz); 7.70 ppm (d, 1H, J=5.0 Hz).

$^{13}$C NMR (DMSO-d$_6$): 31.32 ppm; 101.98 ppm (d, J=65.2 Hz); 104.82 ppm (d, J=23.5 Hz); 110.16 ppm (d, J=26.1 Hz); 111.59 ppm (d, J=10.1 Hz); 127.49 ppm; 127.54 ppm; 128.53 ppm; 133.26 ppm; 135.14 ppm; 135.64 ppm; 157.7 ppm (d, J=233.4 Hz).

MS (EI, 70 eV): 231 (100, M$^+$); 216 (14); 107 (12); 45 (20).

EXAMPLE 3

Preparation of 4- and 6-Fluoro-1-methyl-2-(2'-thienyl)indole

2-Acetylthiophene 3-fluorophenylhydrazone

This compound is prepared from commercial 3-fluorophenylhydrazine hydrochloride (Aldrich) and from commercial 2-acetylthiophene (Aldrich), according to the procedure 1.

Yield: 42%.
Physical characteristics:

$^1$H NMR (DMSO-d$_6$): 2.26 ppm (s, 3H); 6.52 ppm (td, 1H, J=2.5–8.5–8.5 Hz); 6.84–7.0 ppm (m, 2H); 7.03 ppm (dd, 1H, J=3.5–5.0 Hz); 7.16–7.30 ppm (m, 1H); 7.28 ppm (dd, 1H, J=1.0–3.5 Hz); 7.43 ppm (dd, 1H, J=1.0–5.0 Hz)); 9.50 ppm (bs, 1H).

4- and 6-Fluoro-2-(2'-thienyl)indole

These compounds are prepared from the 2-acetylthiophene 3-fluorophenylhydrazone obtained above, according to the procedure 1.

Yield: 74% of a 1:1 mixture of the two isomers.
Physical characteristics:

$^1$H NMR (DMSO-d$_6$): 1:1 mixture of the two isomers: 6.68 ppm (d, 0.5H, J=1 Hz); 6.72 ppm (m, 0.5H); 6.76–6.91 ppm (m, 1H); 7.0–7.24 ppm (m, 2.5H); 7.44–7.60 ppm (m, 2.5H); 11.7 ppm (bs, 0.5H); 11.9 ppm (bs, 0.5H).

4- and 6-Fluoro-1-methyl-2-(2'-thienyl)indole

These compounds are prepared from the mixture of 4- and 6-fluoro-2-(2'-thienyl)indole obtained above, according to the procedure 1.

Yield: 68%.

4-Fluoro-1-methyl-2-(2'-thienyl)indole

Physical characteristics:

Melting point: 86° C.

$^1$H NMR (DMSO-d$_6$): 3.85 ppm (s, 3H); 6.70 ppm (s, 1H); 6.85 ppm (dd, 1H, J=8.0–10.0 Hz); 7.17 ppm (td, 1H, J=5.0–8.0–8.0 Hz); 7.24 ppm (dd, 1H, J=3.5–5.0 Hz); 7.37 ppm (d, 1H, J=8.5 Hz); 7.47 ppm (d, 1H, J=3.5 Hz); 7.52 ppm (d, 1H, J=5.0 Hz).

$^{13}$C NMR (DMSO-d$_6$): 31.72 ppm; 99.06 ppm; 105.21 ppm (d, J=19.2 Hz); 106.17 ppm (d, J=3.5 Hz); 122.97 ppm (d, J=7.4 Hz); 127.03 ppm; 127.06 ppm; 127.66 ppm; 128.17 ppm; 128.21 ppm; 134.28 ppm (d, J=24.1 Hz); 141.43 ppm (d, J=12 Hz); 156.77 ppm (d, J=248 Hz).

MS (EI, 70 eV): 231 (100, M$^+$); 216 (8); 198 (10); 185 (14); 172 (10); 45 (20).

6-Fluoro-1-methyl-2-(2'-thienyl)indole

Physical characteristics:

Melting point: 74°–75° C.

$^1$H NMR (DMSO-d$_6$): 3.80 ppm (s, 3H); 6.92 ppm (td, 1H, J=2.5–9.0–9.0 Hz); 7.21 ppm (dd, 1H, J=3.5–5.0 Hz); 7.34–7.44 ppm (m, 2H); 7.54 ppm (dd, 1H, J=5.5–8.5 Hz); 7.67 ppm (d, 1H; J=5.0 Hz).

$^{13}$C NMR (DMSO-d$_6$): 31.44 ppm; 96.49 ppm (d, J=26.5 Hz); 103.26 ppm; 109.23 ppm (d, J=24.5 Hz); 121.84 ppm (d, J=10.0 Hz); 124.67 ppm; 126.76 ppm; 127.29 ppm; 128.20 ppm; 134.40 ppm; 134.99 ppm (d, J=4.0 Hz)); 139.00 ppm (d, J=11.8 Hz); 160.66 ppm (d, J=238.9 Hz).

MS (EI, 71 eV): 231 (100, M$^+$); 216 (10); 185 (12); 172 (14); 58 (50); 45 (60).

EXAMPLE 4

Preparation of 1-Methyl-2-(2'-selenophenyl)indole

2-Acetylselenophene phenylhydrazone

This compound is prepared from commercial phenylhydrazine hydrochloride (Aldrich) and 2-acetylselenophene, which is itself obtained according to the procedure described by S. Umezawa (reference 18).

Yield: 82%.
Physical characteristics:

$^1$H NMR (DMSO-d$_6$): 2.25 ppm (s, 3H); 6.75 ppm (tt, 1H, J=1.5–1.5–7.0–7.0 Hz); 7.08–7.28 ppm (m, 4H); 7.24 ppm (dd, 1H, J=3.5–5.5 Hz); 7.35 ppm (dd, 1H, J=1.0–3.5 Hz); 7.95 ppm (dd, 1H, J=1.0–5.5 Hz); 9.30 ppm (bs, 1H).

2-(2'-Selenophenyl)indole

This compound is prepared from the 2-acetyl-selenophene phenylhydrazone obtained above, according to the procedure 1.

Yield: 61%.
Physical characteristics:

$^1$H NMR (DMSO-d$_6$): 6.66 ppm (d, 1H, J=1.5 Hz); 6.97 ppm (m, 1H); 7.09 ppm (m, 1H); 7.33 ppm (dd, 1H, J=4.0–5.5 Hz); 7.34 ppm (d, 1H, J=8.0 Hz); 7.48 ppm (d, 1H, J=8.0 Hz); 7.65 ppm (dd, 1H, J=1.0–4.0 Hz); 8.11 ppm (dd, 1H, J=1.0–5.5 Hz); 11.51 ppm (bs, 1H).

$^{13}$C NMR (DMSO-d$_6$): 99.92 ppm; 111.39 ppm; 119.82 ppm; 120.15 ppm; 122.11 ppm; 125.68 ppm; 128.87 ppm; 130.66 ppm; 130.98 ppm; 134.73 ppm; 137.21 ppm; 140.99 ppm.

MS (EI, 70 eV): 247 (100, M$^+$); 167 (80); 139 (40); 127 (15); 113 (15); 89 (30); 63 (40); 43 (45).

1-Methyl-2-(2'-selenophenyl)indole

This compound is prepared from the 2-(2'-selenophenyl)indole obtained above, according to the procedure 1.

Yield: 90%.
Physical characteristics:

$^1$H NMR (DMSO-d$_6$): 3.83 ppm (s, 3H); 6.65 ppm (s, 1H); 7.05 ppm (m, 1H); 7.20 ppm (m, 1H); 7.43 ppm (dd, 1H, J=3.5–5.0 Hz); 7.45–7.57 ppm (m, 3H); 8.28 ppm (dd, 1H, J=1.0–5.0 Hz).

$^{13}$C NMR (DMSO-d$_6$): 31.04 ppm; 102.53 ppm; 110.41 ppm; 120.09 ppm; 120.33 ppm; 122.15 ppm; 127.50 ppm; 129.24 ppm; 130.76 ppm; 133.29 ppm; 135.89 ppm; 138.47 ppm; 139.06 ppm.

MS (EI, 70 eV): 261 (100, M$^+$); 180 (70); 167 (20); 152 (25); 63 (30).

EXAMPLE 5

Preparation of 1-methyl-2-phenylindole

This compound is obtained from commercial 2-phenylindole (Lancaster) by an alkylation reaction according to the procedure 1.

Yield: 87%.
Physical characteristics:
Melting point: 100°–101° C.

$^1$H NMR (DMSO-d$_6$): 3.75 ppm (s, 3H); 6.57 ppm (s, 1H); 7.07 ppm (m, 1H); 7.19 ppm (m, 1H); 7.40–7.64 ppm (m, 6H).

$^{13}$C NMR (DMSO-d$_6$): 31.05 ppm; 101.43 ppm; 110.37 ppm; 119.90 ppm; 120.40 ppm; 121.75 ppm; 127.78 ppm; 128.21 ppm; 128.97 ppm; 129.30 ppm; 132.54 ppm; 138.49 ppm; 141.53 ppm.

MS (EI, 70 eV): 207 (100, M$^+$).

EXAMPLE 6

Preparation of sodium 5-(1-methyl-2-phenylindolyl) sulfonate

This compound is prepared from 1-methyl-2-phenylindole obtained above, according to the standard procedure (reference 15).

Yield: 24%.
Physical characteristics:
Melting point: >360° C.

$^1$H NMR (D$_2$O): 3.18 ppm (s, 3H); 6.21 ppm (s, 1H); 7.0–7.20 ppm (m, 6H); 7.55 ppm (dd, 1H, J=1.5–8.0 Hz); 7.90 ppm (d, 1H, J=1.5 Hz).

$^{13}$C NMR (D$_2$O): 32.94 ppm ; 104.62 ppm; 113.00 ppm; 120.89 ppm; 121.69 ppm; 129.07 ppm; 130.51 ppm; 130.98 ppm; 131.38 ppm; 134.23 ppm; 137.22 ppm; 141.66 ppm; 145.09 ppm.

EXAMPLE 7

Preparation of sodium 5,5'-[1,1'-dimethyl-2,2'-(m-phenylene)diindolyl]-disulfonate This compound is prepared from 1,1'-dimethyl-2,2'-(m-phenylene)diindole obtained in Example 1, according to the standard procedure (reference 15).

Yield: 48%.
Physical characteristics:
Melting point: >360° C.

$^1$H NMR (D$_2$O): 3.26 ppm (s, 6H); 6.13 ppm (s, 2H); 6.77 ppm (bs, 1H); 7.16–7.34 ppm (m, 5H); 7.55 ppm (dd, 2H, J=1.5–8.5 Hz); 7.95 ppm (d, 2H, J=1.5 Hz). $^{13}$C NMR (D$_2$O): 33.11 ppm; 104.85 ppm; 113.17 ppm; 120.77 ppm; 121.57 ppm; 128.89 ppm; 128.98 ppm; 131.06 ppm; 131.59 ppm; 134.33 ppm; 136.87 ppm; 141.71 ppm; 144.71 ppm; 144.76 ppm; 144.85 ppm.

MS (FAB, glycerol): 563 (20); 541 (M+H$^+$, 20); 461 (20); 265 (100).

B. Examples using the procedure 2:

EXAMPLE 8

Preparation of 1-methyl-2-(2'-thienyl)indole

2-[2'-(2''-thienyl)ethynyl]aniline

To a solution of 2-ethynylaniline (440 mg; 3.8 mmol) and 2-iodothiophene (798 mg; 3.8 mmol) in 10 ml of diethylamine/dimethylformamide (4:1) are added tetrakis (triphenylphosphine)palladium (420 mg; 38 µmol) and cuprous iodide (14.4 mg; 76 µmol). The reaction mixture is stirred for 6 h at room temperature and then 100 ml of water and 100 ml of tert-butyl methyl ether are added thereto. The organic phase is dried over sodium sulfate and filtered. The solvent is evaporated off under reduced pressure. The desired product is obtained in crystalline form after purification by liquid chromatography on a silica-column (eluent: hexane/ethyl acetate 9:1).

Yield: 560 mg; 74%.
Physical characteristics:
$^1$H NMR (CDCl$_3$): 4.23 ppm (bs, 2H); 6.70 ppm (m, 2H); 7.00 ppm (dd, 1H, J=3.5–5.0 Hz); 7.13 ppm (m, 1H); 7.22–7.38 ppm (m, 3H).

2-(2'-Thienyl)indole

The product obtained above (560 mg; 2.8 mmol) is dissolved in 15 ml of acetonitrile and then palladium chloride (25 mg; 0.14 mmol) is added. The reaction mixture is heated for 3 h at a reflux. The solvent is evaporated off under reduced pressure. The desired product is obtained in the form of slightly yellowish powder, after purification by liquid chromatography on a silica column (eluent: hexane/ethyl acetate 9:1).

Yield: 400 mg; 71%.
Physical characteristics:
Melting point: 168° C.

$^1$H NMR (DMSO-d$_6$): 6.65 ppm (s, 1H); 6.92 ppm (td, 1H, J=1.0–7.0–7.0 Hz); 7.09 ppm (td, 1H, J=1.0–7.0–7.0 Hz); 7.36 ppm (d, 1H, J=7.0 Hz); 7.46–7.55 ppm (m, 3H); 11.55 ppm (bs, 1H).

$^{13}$C NMR (DMSO-d$_6$): 98.96 ppm; 111.40 ppm; 119.84 ppm; 120.20 ppm; 122.04 ppm; 123.79 ppm; 125.41 ppm; 128.43 ppm; 128.80 ppm; 132.22 ppm; 135.85 ppm; 137.13 ppm.

MS (IE, 70 eV): 199 (100, M$^+$); 171 (10); 154 (10).

1-Methyl-2-(2'-thienyl)indole

Powdered potassiumhydroxide (2.52 g; 45 mmol) is added to a solution of 2-(2'-thienyl)indole (3.0 g; 15 mmol) in 30 ml of dimethyl sulfoxide. The reaction mixture is stirred for 14 h at room temperature. Methyl sulfate (6.6 g; 52.5 mmol) is then added. After 15 minutes, 100 ml of water are added to the reaction mixture. The product is extracted with 200 ml of ethyl acetate. The organic phase is washed with 2×100 ml of saturated sodium chloride solution and then dried over magnesium sulfate. The desired product is obtained after purification by liquid chromatography on a silica column (eluent: cyclohexane/ethyl acetate 30:1) and recrystallization (hexane/isopropanol 2:1).

Yield: 2.62 g; 82%.
Physical characteristics:
Melting point: 58° C.

$^1$H NMR (DMSO-d$_6$): 3.87 ppm (s, 3H); 6.65 ppm (s, 1H); 7.05 ppm (t, 1H, J=8.0 Hz); 7.19 ppm (t, 1H, J=8.0 Hz); 7.23 ppm (dd, 1H J=3.5–5.0 Hz); 7.41 ppm (d, 1H, J=3.5 Hz); 7.50 ppm (d, 1H, J=7.0 Hz); 7.55 ppm (d, 1H, J=7.0 Hz); 7.68 ppm (d, 1H, J=5.0 Hz).

$^{13}$C NMR (DMSO-d$_6$): 31.03 ppm; 102.04 ppm; 110.39 ppm; 120.08 ppm; 120.37 ppm; 122.14 ppm; 127.17 ppm; 127.43 ppm; 128.53 ppm; 133.65 ppm; 133.87 ppm; 138.37 ppm.

MS (EI, 70 eV): 213 (100, M$^+$); 167 (15); 154 (15); 89 (20); 58 (60); 45 (45); 39 (25).

EXAMPLE 9

Preparation of 1-methyl-5-nitro-2-(2'-thienyl)indole

5-Nitro-2-(2'-thienyl)indole

This compound is obtained by nitration of 2-(2'-thienyl) indole according to the procedure described in reference 19.

Yield: 53%.
Physical characteristics:
¹H NMR (DMSO-d₆): 6.96 ppm (s, 1H); 7.20 ppm (dd, 1H, J=3.5–5.0 Hz); 7.52 ppm (d, 1H, J=9.0 Hz); 7.60–7.66 ppm (m, 2H); 8.0 ppm (dd, 1H, J=2.0–9.0 Hz); 8.51 ppm (d, J=2 Hz); 12.33 (bs, 1H).

1-Methyl-5-nitro-2-(2'-thienyl)indole

This compound is obtained from 5-nitro-2-(2'-thienyl) indole obtained above by an alkylation reaction according to the procedure 1.

Yield: 83%.

¹H NMR (DMSO-d₆): 3.98 ppm (s, 3H); 6.98 ppm (s, 1H); 7.27 ppm (dd, 1H, J=3.5–5.5 Hz); 7.53 ppm (d, 1H, J=3.5 Hz); 7.74 ppm (d, 1H, J=9.0 Hz); 7.78 ppm (d, 1H, J=5.5 Hz); 8.07 ppm (dd, 1H, J=2.0–9.0 Hz); 8.57 ppm (d, 1H, J=2.0 Hz).

EXAMPLE 10

Preparation of 5-amino-1-methyl-2-(2'-thienyl) indole

This compound is obtained from-5-nitro-2-(2'-thienyl) indole obtained in Example 9 by reduction, using tin chloride ($SnCl_2$).

Yield: 63%.
Physical characteristics:
¹H NMR (DMSO-d₆): 3.72 ppm (d, 3H, J=1.5 Hz); 4.60 ppm (bs, 2H); 6.35 ppm (s, 1H); 6.58 ppm (d, 1H, J=8.5 Hz); 6.65 ppm (s, 1H); 7.14–7.22 ppm (m, 3H); 7.32 ppm (m, 1H); 7.61 ppm (m, 1H).

MS (EI, 70 eV): 228 (100, M⁺); 213 (30); 114 (10).

EXAMPLE 11

Preparation of disodium 2-{1'-[2'-(2"-thienyl) indolyl]}ethylphosphonate 1-(2'-Diethoxyphosphono)ethyl-2-(2"-thienyl)indole This compound is obtained by alkylation of 2-(2'-thienyl) indole using commercial vinyl diethoxyphosphonate (Aldrich), according to the alkylation procedure used in the above examples.

Yield: 53%.
Physical characteristics:
¹H NMR (DMSO-d₆): 1.17 ppm (t, 6H, J=7.0 Hz); 2.17 ppm (m, 2H); 3.94 ppm (m, 4H); 4.46 ppm (m, 2H); 6.66 ppm (s, 1H); 7.08 ppm (t, 1H, J=7.5 Hz); 7.17–7.27 ppm (m, 1H); 7.47 ppm (d, 1H, J=7.5 Hz); 7.57 ppm (d, 1H, J=7.5 HZ); 7.72 (d, 1H, J=5.0 Hz).

Disodium 2-{[1'-[2'-(2"-thienyl)indolyl]}ethylphosphonate

This compound is obtained by hydrolysis of 1-(2'-diethoxyphosphono)ethyl-2-(2"-thienyl)indoleabove, using trimethylsilyl bromide.

Yield: 99%.
Physical characteristics:
¹H NMR (D₂O): 1.85 ppm (m, 2H); 4.42 ppm (m, 2H); 6.48 ppm (s, 1H); 7.02 ppm (t, 1H, J=7.5 Hz); 7.09 ppm (dd, 1H, J=3.5–5.0 Hz); 7.16–7.26 ppm (m, 2H); 7.39 ppm (dd, 1H, J=1.0–5.0 Hz); 7.45 ppm (d, 1H; J=7.5 Hz); 7.53 ppm (d, 1H, J=7.5 Hz).

¹³C NMR (D₂O): 36.75 ppm (d, J=125 Hz); 42.94 ppm; 105.01 ppm; 113.35 ppm; 123.10 ppm; 123.48 ppm; 125.16 ppm; 129.79 ppm; 130.38 ppm; 131.10 ppm; 136.10 ppm; 136.55 ppm; 139.99 ppm.

MS (FAB, glycerol): 374 (55); 352 (30, M+H⁺); 165 (25); 148 (30); 137 (50); 122 (70); 108 (100).

C. Example using the procedure 3

EXAMPLE 12

Preparation of 1-methyl-2-phenylbenzo(f)indole

3-Amino-2-bromonaphthalene

This compound is obtained from commercial bis (hexachlorocyclopentadienyl)-2-bromo-3-nitronaphthalene (Aldrich), according to the procedure described in reference 20.

Yield: 71%.
Physical characteristics:
¹H NMR (CDCl₃): 4.25 ppm (bs, 2H); 7.09 ppm (s, 1H); 7.22 ppm (t, 1H, J=7.5 Hz); 7.36 ppm (t, 1H, J=7.5 Hz); 7.56 ppm (d, 1H, J=7.5 Hz); 7.60 ppm (d, 1H, J=7.5 Hz); 7.96 ppm (s, 1H).

2-Bromo-3-(ethoxycarbonyl)aminonaphthalene

This compound is prepared from 3-amino-2-bromonaphthalene obtained above and commercial ethyl chloroformate (Aldrich), according to the procedure 3.

Yield: 75%.
Physical characteristics:
¹H NMR (CDCl₃): 1.36 ppm (t, 3H, J=7 Hz); 4.28 ppm (q, 2H, J=7 Hz); 7.29 ppm (bs, 1H); 7.42 ppm (m, 2H); 7.66 ppm (d, 1H, J=8 Hz); 7.78 ppm (d, 1H, J=8 Hz); 8.05 ppm (s, 1H); 8.59 ppm (s,1H).

MS (EI, 70 eV): 293 (32, M⁺); 249 (12); 234 (25); 223 (35); 214 (14); 193 (70); 186 (77); 140 (35); 114 (100); 87 (28); 63 (50).

2-(Ethoxycarbonyl)amino-3-(2'-phenylethynyl) naphthalene

This compound is prepared from 2-bromo-3-(ethoxycarbonyl)aminonaphthalene obtained above, according to the procedure 3.

Yield: 83%.
Physical characteristics:
¹H NMR (CDCl₃): 1.37 ppm (t, 3H, J=7 Hz); 4.30 ppm (q, 2H, J=7 Hz); 7.32–7.50 ppm (m, 5H); 7.54–7.63 ppm (m, 3H); 7.72 ppm (d, 1H, J=8 Hz); 7.78 ppm (d, 1H, J=8 Hz); 8.02 ppm (s, 1H); 8.58 ppm (s, 1H).

2-Phenyl-1(H)-benzo(f)indole

This compound is prepared from 2-(ethoxycarbonyl) amino-3-(2'-phenylethynyl)naphthalene obtained above, according to the procedure 3.

Yield: 34%.
Physical characteristics:
¹H NMR (DMSO-d₆): 7.08 ppm (d, 1H, J=1 Hz); 7.27 ppm (m, 2H); 7.40 ppm (d, 1H, J=7 Hz); 7.51 ppm (t, 2H, J=7.5 Hz); 7.85 ppm (s, 1H); 7.87–8.09 ppm (m, 4H); 8.07 ppm (s, 1H); 11.54 ppm (bs, 1H).

MS (EI, 70 eV): 243 (100, M⁺); 215 (18); 139 (38); 87 (13); 77 (25); 63 (14).

1-Methyl -2-phenylbenzo(f)indole

This compound is prepared from 2-phenyl-1(H)-benzo(f) indole by alkylation, as described in the procedure 1.

Yield: 72%.
Physical characteristics:

$^1$H NMR (DMSO-D$_6$): 3.85 ppm (s, 3H); 6.75 ppm (s, 1H); 7.33 ppm (m, 2H); 7.47–7.62 ppm (m, 3H); 7.65–7.72 ppm (m, 2H); 7.91–8.02 ppm (m, 3H); 8.13 ppm (s, 1H).

MS (EI, 70 eV): 257 (100, M$^+$); 215 (12); 77 (11).

EXAMPLE 13

Preparation of 1-methyl-2-phenylbenzo(f)indole-5,7-disulfonic acid

The 1-methyl-2-phenylbenzo(f)indole derivative, previously obtained, (0.15 g; 0.58 mmol) is treated with 1 ml oleum (20% SO$_3$) for 1 hour at 0° C. Then, 2 ml of cold water is added to the reaction medium, slowly and dropwise. After a filtration of the suspension thus obtained, and washing with 200 µl of cold water, the mixture of the two isomers, 1-methyl-2-phenylbenzo(f)indole-5,7-disulfonic acid and 1-methyl-2-phenylbenzo(f)indole-6,8-disulfonic acid, is obtained in the form of a very hygroscopic yellow powder. The yield of the mixture is 88%.

The desired product is obtained after purification by liquid chromatography on a column, with a yield of 35%.
Physical characteristics:

$^1$H NMR (D$_2$O+NaOD): 3.44 ppm (s, 3H); 7.30 ppm (m, 5H); 7.84 ppm (s, 1H); 8.21 ppm (m, 1H); 8.45 ppm (m, 1H); 8.80 ppm (s, 1H).

MS (negative ion FAB; triethanolamine): 416 (M—H; 50%); 336 (20%); 195 (100%).

EXAMPLE 14

Preparation of 1-methyl-2-phenlbenzo(f)indole-6,8-disulfonic acid

This derivative is obtained from the preceding mixture, after purification by liquid chromatography on column, with a yield of 53%.
Physical characteristics:

$^1$H NMR (D$_2$O+NaOD) 3.61 ppm (s, 3H); 7.30 ppm (m, 5H); 8.08 ppm (s, 1H); 8.26 ppm (m, 1H); 8.43 ppm (m, 1H); 8.50 ppm (s, 1H).

MS (negative ion FAB; triethanolamine): 416 (M—H; 50%); 336 (20%); 195 (100%).

EXAMPLE 15

Preparation of the disodium salt of 1-methyl-2-phenylbenzo(f)indole-5,7-disulfonic acid 1-Methyl-2-phenylbenzo(f)indole-5,7-disulfonic acid (75 mg; 0.18 mmol) is treated with 7.5 ml of a hot saturated solution of sodium chloride. The desired product is obtained after cooling to room temperature, filtration and washing with 500 µl of a saturated solution of sodium chloride diluted to ⅕th in the form of flat, slightly yellow and fluorescent crystals. Yield: 78%.
Physical characteristics:
m.p.: >360° C.

$^1$H NMR (D$_2$O): 3.60 ppm (s, 3H); 6.65 ppm (bs, 1H); 7.38–7.50 ppm (m, 5H); 7.98 ppm (s,1H); 8.19 ppm (m, 1H), 8.50 ppm (s, 1H); 8.82 ppm (s,1H)

MS (negative ion FAB; triethanolamine): 496 (20%); 438 (35%); 206 (100%); 194 (85%); 171 (46%); 113 (45%).

EXAMPLE 16

Preparation of the disodium salt of 1-methyl-2-phenylbenzo(f)indole-6,8-disulfonic acid 1-Methyl-2-phenylbenzo(f)indole-6,8-disulfonic acid (80 mg; 0.19 mmol) is treated with 8.0 ml of a hot saturated solution of sodium chloride. The desired product is obtained after cooling to room temperature, filtration and washing with 500 µl of a saturated solution of sodium chloride diluted to ⅕th in the form of flat, slightly yellow and fluorescent crystals. Yield: 82%
Physical characteristics:
m.p.: >360° C.

$^1$H NMR (D$_2$O): 3.73 ppm (s, 3H); 6.61 ppm (bs,1H); 7.38–7.50 ppm (m, 5H); 8.23 ppm (bs, 2H); 8.49 ppm (bs,1H); 8.54 ppm (s, 1H)

MS (negative ion FAB; triethanolamine): 496 (20%); 438 (35%); 206 (100%); 194 (85%); 171 (46%); 113 (45%).

II. Example of implementation of the process according to the invention:

EXAMPLE 17

Colorimetric assay of lipid peroxidation using 1-methyl-2-phenylindole (compound of Example 5)

1-Methyl-2-phenylindole (hereinafter called "chromogenic reagent R1" or more simply "reagent R1") reacts with MDA and 4-hydroxyalkenals at 45° C. Condensation of one molecule of MDA or 4-hydroxyalkenal with two molecules of reagent R1 produces a stable chromophore for which the maximum absorbance wavelength, characteristic of the reagent R1, is equal to 586 nm. For this reason, this method will hereinafter be called "LPO-586 method".

In the case of MDA, this chromophore has the formula:

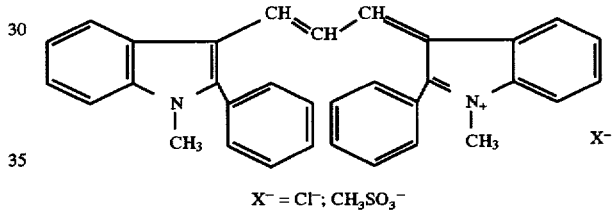

$$X^- = Cl^-; CH_3SO_3^-$$

The LPO-586 method makes possible an assay which is specific for MDA and 4-hydroxy-2-enaldehydes on an aqueous test sample. Its simplicity of implementation is particularly well suited to the measurement of lipid peroxidation on large series of samples.

Most of the interferences known for other colorimetric assay methods are eliminated in the LPO-586 method, which is reflected in a much higher specificity and sensitivity.

A variant of the LPO-586 method makes it possible to measure specifically the amount of MDA in a sample containing 4-hydroxy-2-enaldehydes (see below).

The specific measurement of these two parameters in the same sample makes it possible to evaluate the possible enzymatic origin of MDA (for example biosynthesis of thromboxane).

The main reagents used for the implementation of this method may be assembled in a box (in requisite or kit form).

Such a box may, for example, contain the amounts of reagents which make it possible to carry out 100 assays, namely:

Reagent R1: 10.3 mmolar solution of chromogenic reagent R1 in acetonitrile; (3×18 ml).

Reagent R2: 10.4 molar methanesulfonic acid; (3×5.5 ml) containing, where appropriate, 34 µmolar ferric chloride.

Standard solution S1: 10 mmolar solution of 1,1,3,3-tetramethoxypropane in 20 mmolar Tris-HCl buffer, pH 7.4; (1 ml).

Standard solution S2: 10 mmolar solution of 4-hydroxynonenal diethyl acetal in acetonitrile (1 ml).

Note:

1,1,3,3-tetramethoxypropane and 4-hydroxynonenal diethyl acetal are converted in acid medium into MDA and 4-hydroxynonenal respectively.

All these solutions must be packaged in hermetically closed bottles and must be stored between +4 and 10° C. until the expiry date indicated on the box label. They should not be frozen.

After opening and utilization, the carefully stoppered bottles should be stored between +4 and +10° C.

Under these conditions, the solutions may be used for the two months following the date of first opening the bottles.

The equipment used essentially consists of:

an absorption spectrophotometer which enables the absorption to be measured at a wavelength of 586 nm (±4 nm), at an interval of 0 to 2 absorbance units;

1 ml spectrophotometric cells of 1 cm optical path length;

a water bath thermostatted at 45±1° C.

The lipid peroxidation measurement carried out requires that the glassware used has undergone washing with acid (acetic or hydrochloric) and thorough rinsing with very pure deionized water. The single-use test tubes and stoppers must be compatible with the solvents and acids of the box.

All the products (water, buffers and solvents) used for the dilution of the samples or for the measurements must be of ultra-pure quality.

EXPERIMENTAL PROCEDURE

1. Preparation of the final solution of reagent R1.

Immediately before utilization, three volumes of the initial solution of reagent R1 (18 ml) are diluted by addition of one volume (6 ml) of pure methanol.

A solution R1-dil is obtained containing 7.7 mmolar R1 in an acetonitrile/methanol 3:1 (v/v) mixture.

This solution, which is ready to use, should not be stored longer than one day.

2. Assay.

Before each series of measurements, the absorbance zero of the spectrophotometer at 586 nm is adjusted against water.

a) 650 µl of R1-dil solution are distributed into all the test tubes.

b) For each assay:

200 µl of sample are added followed by mixing. The reaction is started by addition of 150 µl of reagent R2 (methanesulfonic acid). Thorough mixing is carried out and then the tubes are carefully stoppered. The reaction mixture is incubated for 40 minutes in a water bath equilibrated at 45° C. The absorbance (A) is measured at 586 nm.

c) For each series of assays, a control sample ([aldehyde] =0) is used in duplicate, whose mean absorbance ($A_o$) will subsequently be subtracted from the absorbance values (A) measured in the presence of each sample to be assayed.

Comments:

The order of addition of the solutions should not be inverted.

The working temperature chosen, 45° C., makes it possible for the reaction to reach a plateau in 40 min.

The intensity of absorbance at 586 nm (A–$A_o$) is a linear function of the concentration of MDA and 4-hydroxyalkenals. It is stable for at least two hours.

3. Calibration:

The standard solutions S1 and S2 make it possible to produce calibration "ranges" for MDA and 4-hydroxynonenal respectively.

Before use, these solutions are diluted to 1/100 (v/v) in the same medium as the sample in order to obtain 100 µmolar concentrations.

The procedure 2 above is followed, replacing the sample by 0 to 200 µl of 100 µmolar standard solution and made up to 200 µl (qs) with medium.

This procedure covers the 0 to 20 µmolar concentration interval in the final reaction medium (spectrophotometer cell).

A least-squares linear regression should show that the absorbance difference (A–$A_o$) is a linear function of the MDA and 4-hydroxynonenal concentration. If this was not the case, it would mean that the reagents used are impure or degraded.

The apparent molar extinction coefficient (E) of the product measured is equal to the slope of this straight regression line.

FIG. 1 annexed shows the kinetics for formation of the adduct of tetramethoxypropane (TMP) with 1-methyl-2-phenylindole (MPI), during incubation at 45° C. with methanesulfonic acid (reagent R2) at a concentration of 15%.

Figure 2:
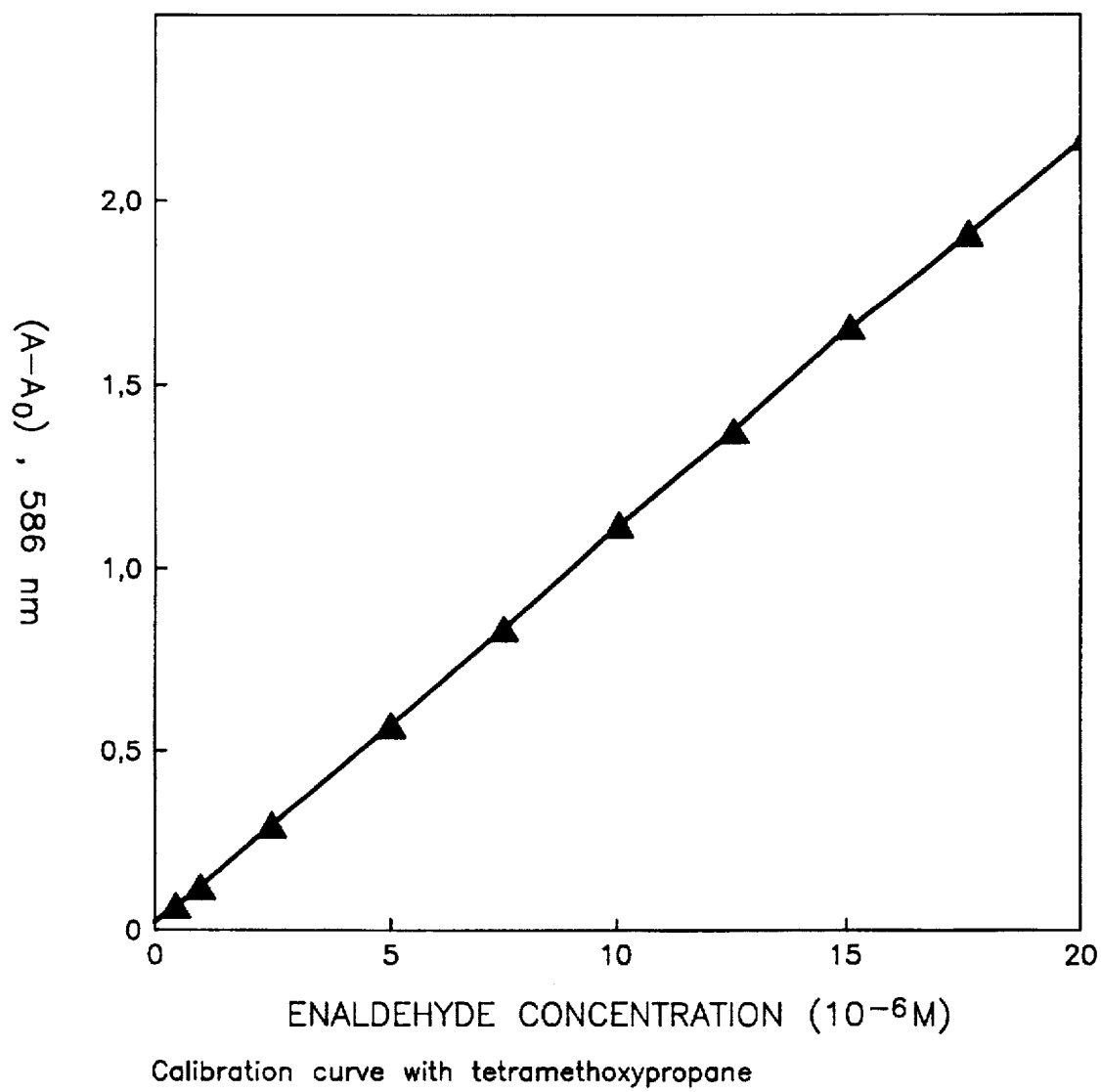
FIG. 2 represents the calibration curve obtained with tetramethoxypropane, which is converted into MDA in acidic medium, established under the following conditions; methanesulfonic acid at a concentration of 15% (v/V), incubation at 45° C. for 40 minutes.
Figure 3:
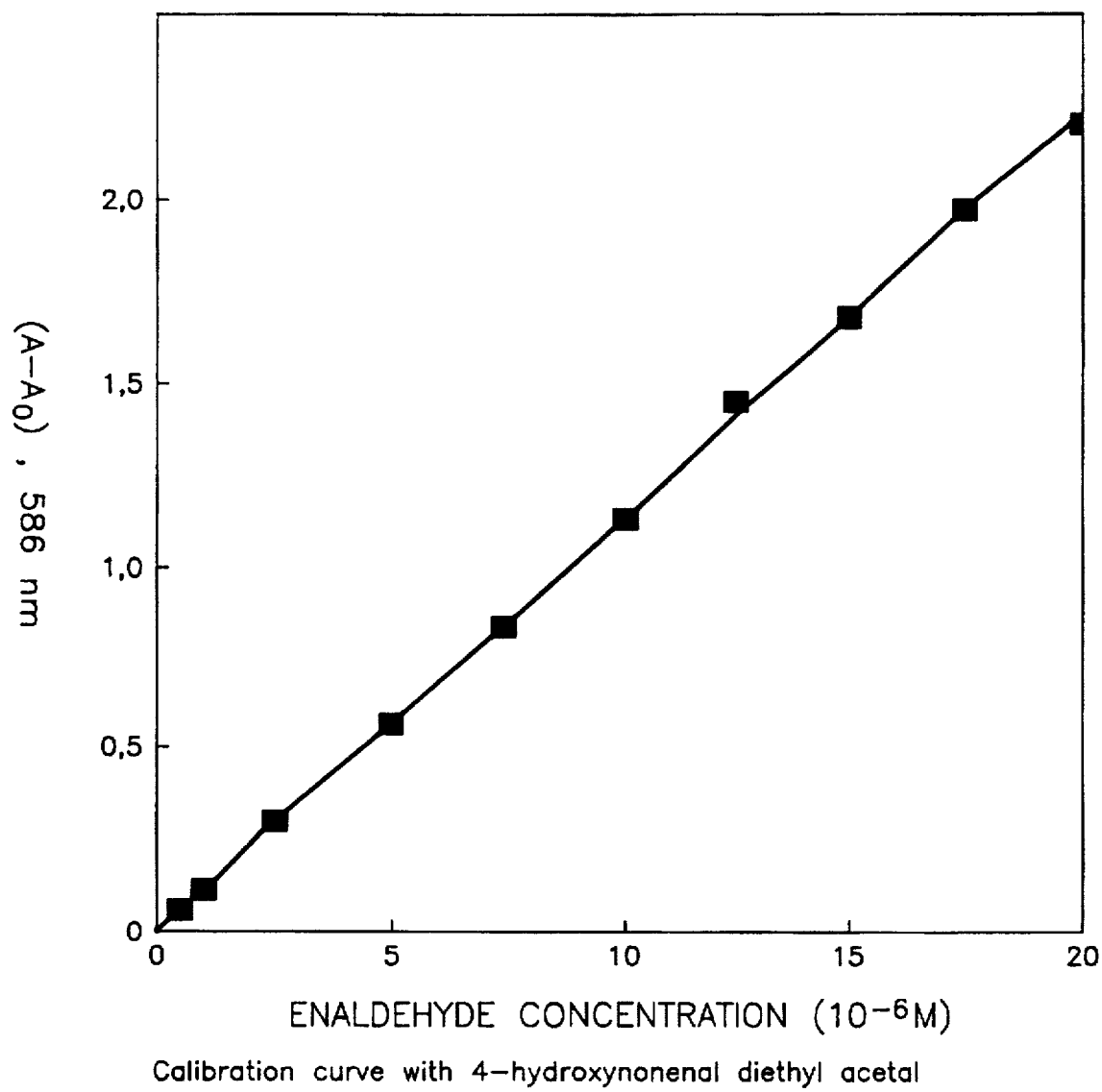
FIG. 3 represents the calibration curve obtained with 4-hydroxynonenal diethyl acetal which is converted into 4-hydroxynonenal in acidic medium, established under the same conditions as FIG. 2.

FIGS. 2 and 3 provide examples of calibration curves. They show that the same molar extinction coefficient (E) is obtained with MDA and 4-hydroxynonenal.

More precisely:

FIG. 2 represents the calibration curve obtained with tetramethoxypropane, which is converted into MDA in acidic medium, established under the following-conditions: methanesulfonic acid at a concentration of 15% (v/v), incubation at 45° C. for 40 minutes;

FIG. 3 represents the calibration curve obtained with 4-hydroxynonenal diethyl acetal, which is converted into 4-hydroxynonenal in acidic medium, established under the same conditions as FIG. 2.

4. Calculation of the concentration.

The following equation gives the molar concentration of MDA and 4-hydroxy-2-enaldehydes in the sample:

$$[MDA+4\text{-hydroxy-2-enaldehydes}]=(A-A_0)\times 5/E$$

Comment: This concentration may also be obtained by plotting A–$A_o$ on the ordinate of the calibration curve used.

5. Sensitivity, precision and reproducibility.

Sensitivity:

The detection threshold is lower than a 0.5 µmolar enaldehyde concentration in the final reaction medium.

In practice, this concentration may be considered as the lower limit of the assay. For a sample volume of 200 µl, the lower assay limit for MDA and/or 4-hydroxyalkenals in the sample thus corresponds to a concentration of 2.5 µmolar.

Precision:

When six measurements are carried out on the same day on four standard concentrations within the 0 to 20 µmolar interval (dilutions prepared at the time of use from a 10 mmolar standard mother solution of acetal stored at +8° C.), the variation coefficients calculated are all lower than 5%.

Reproducibility:

When the above experiment is repeated after an interval of ten days using the same standard mother solution stored at +8° C., the new variation coefficients, calculated from the two series of measurements, remain lower than 5%.

6. Possible interferences.

Lithium or sodium heparinate brings about an artefactual increase of the absorbance intensities at 586 nm.

During incubation at 45° C. a pink coloration of variable intensity develops, due to the formation of compounds whose maximum absorbance wavelength is equal to 505 nm. The absorption at 505 nm generally does not interfere with the chromophore absorption at 586 nm. Comments:

The samples may in particular be diluted in the following media: $H_2OO$; 20 mmolar Tris-HCl buffer, pH 7.4; 50 mmolar Tris-HCl buffer, pH 7.6, in the presence or absence of 0.1% of Lubrol®.

Any modification of the assay parameters, such as temperature, buffer, pH or volume withdrawn, is likely to bring about modifications.

EXAMPLES OF ASSAYS ON BIOLOGICAL SAMPLES (total enaldehydes)

1. Plasma.

A 3 ml blood sample is placed in a tube containing 48 µl of 0.17 molar tripotassium EDTA. After centrifuging at 1700 ×g and 4° C. for 10 minutes the plasma is separated from the erythrocyte pellet.

The assay must be carried out within the following hour, the plasma having been maintained between 0° and 4° C.

The assay is carried out on 200 µl of plasma, under the conditions indicated above. After incubation for 40 minutes at 45° C. in the presence of the reagent R2, the plasma is cooled on ice, centrifuged for 10 minutes at 2500×g and 4° C., and the absorbance (A) of the supernatant is measured at 586 nm.

The control tests ([aldehyde]=0) may be carried out by replacing the plasma by water. Their average gives the value $A_0$.

The total concentration of MDA and enaldehydes is determined using these measurements, as explained above.

2. Tissue homogenate.
Example: rat brain homogenate.

The homogenate may be produced at 1/10 (g/ml) in 20 mmolar Tris-HCl buffer, pH 7.4.

The assay is carried out on the total homogenate or on a low-speed centrifugation supernatant (1700×g). The assay is carried out as described for the plasma, with a test amount of 200 µl.

For a very peroxidized homogenate, the test amount is reduced and it is made up to 200 µl with the abovementioned buffer.

SPECIFIC ASSAY OF THE MDA

If, in the procedure described above, the methane-sulfonic acid (reagent R2) is replaced by the same volume of hydrochloric acid at a concentration of 37%, the reaction plateau is reached at the end of 60 min and a measurement which is specific for the MDA at 586 nm is obtained.

Figure 4:
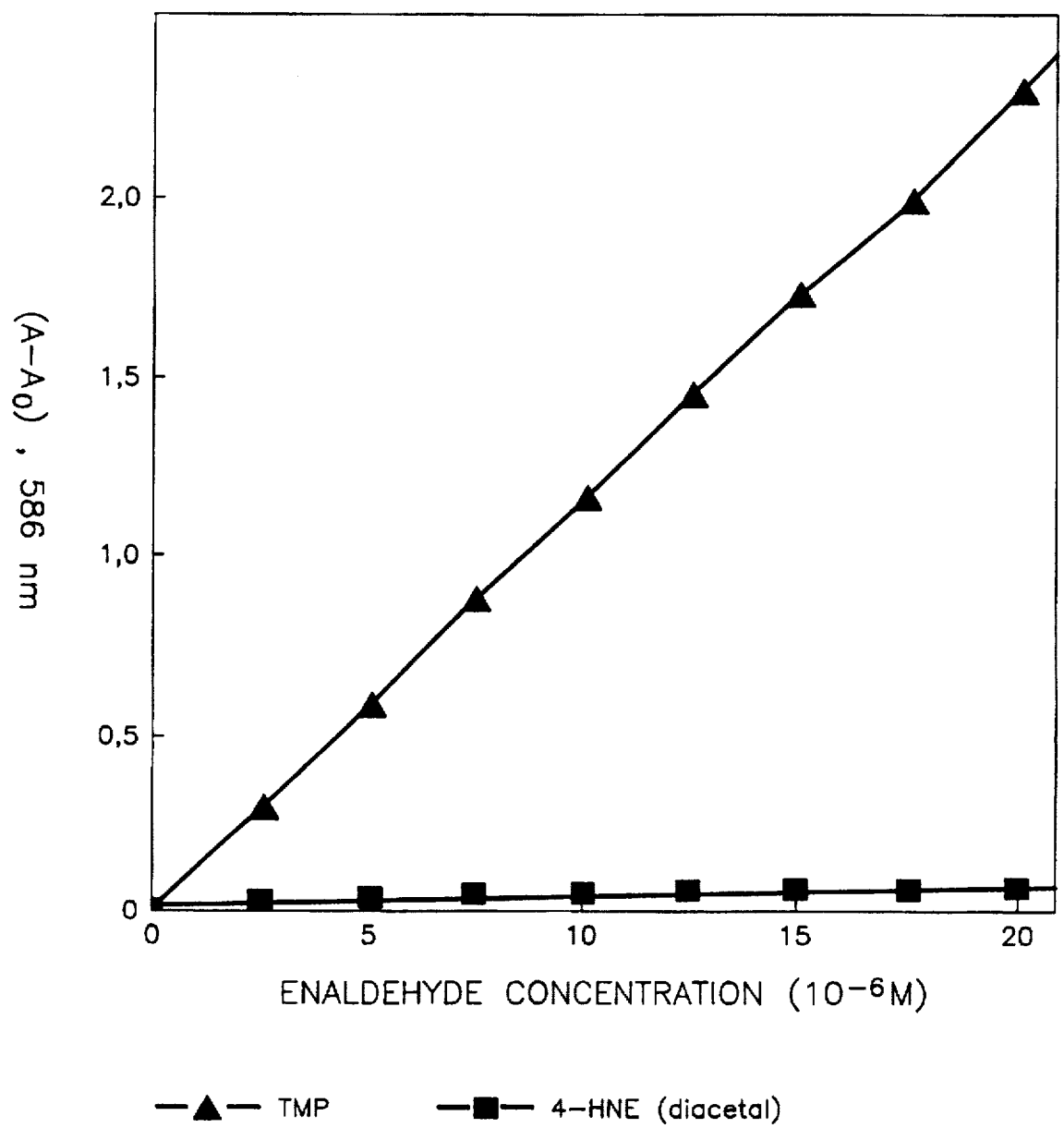
FIG. 4 represents the calibration curve obtained after incubation in presence of HCl at a concentration of 15% (v/v) at 45° C., for 60 minutes, respectively obtained with tetramethoxypropane (TMP), the line linking the triangles, and with 4-hydroxynonenal diacetal (diethyl acetal), in abbreviation 4-HNE, the line linking the squares.

FIG. 4 provides an example of the calibration curve obtained under these conditions and shows that the reactivity of 4-HNE is virtually negligible under these conditions.

More precisely. FIG. 4 represents the calibration curve obtained with tetramethoxypropane (TMP), on the one hand with 4-hydroxynonenal diacetal (diethyl acetal) |4-HNE (diacetal)|, and on the other hand after incubation in the presence of HCl at a concentration of 15% (v/v), at 45° C., for 60 minutes.

Combination of the procedures described above (two test samples and two distinct assays) makes it possible to calculate the concentrations of, on the one hand, the previously defined enaldehydes and, on the other hand, MDA.

The apparent molar extinction coefficient (E) obtained from MDA is the same in the two procedures.

REFERENCES

1. ESTERBAUER H. and CHEESEMAN K. H., (1990). Determination of aldehydic lipid peroxidation products: malonaldehyde and 4-hydroxynonenal; Meth. Enzymol., 189, 407–21.
2. DRAPER H. H. and HADLEY M. (1990). Malondialdehyde determination as index of lipid peroxidation; Meth. Enzymol., 186, 421–431.
3. FRANKEL E. N. and NEFF. W. E. (1983). Formation of malonaldehyde from lipid oxidation products; Biochim. Biophys. Acta, 754, 264–270.
4. HECKER M. et al., (1987). Products, kinetics and substrate specificity of homogeneous thromboxane synthetase from human platelets: development of a novel enzyme assay, Arch. Biochem. Biophys., 254, 124.
5. JANERO D. R. (1990). Malondialdehyde and thiobarbituric acid-reactivity as diagnostic indices of lipid peroxidation and peroxidative tissue injury; Free Rad. Biol. Med., 9, 515–540.
6. SAWICKI E. et al., (1963). Comparison of spectrophotometric and spectrofluorometric methods for the determination of malonaldehyde; Anal. Chem., 55,199–205;
7. H. SCHERZ et al., Mikrochim. Acta, 1967, 915.
8. KNIGHT J. A. et al., (1988). Specificity of the thiobarbituric acid reaction: its use in studies of lipid peroxidation; Clin. Chem., 34, 2433–2438.
9. KOSUGI H. and KIKUGAWA K. (1986). Reaction of thiobarbituric acid with saturated aldehydes; Lipids, 21, 537–542.
10. KOSUGI H. and KIKUGAWA K. (1989). Potential thiobarbituric acid-reactive substances in peroxidized lipids; Free Rad. Biol. Med., 7, 205–207.
11. GUTTERIDGE J. MC. (1984). Reactivity of hydroxyl and hydroxyl-like radicals discriminated by release of thiobarbituric acid-reactive material from deoxy sugars, nucleosides and benzoate; Biochem. J., 224, 761–767.
12. MATSUO T. et al., (1987). Production of a malonaldehyde-like compound from the reaction of peroxide with sugar in acidic solution; Agric. Biol. Chem., 51, 2579–80.
13. ESTERBAUER H. et al., (1986). Studies on the mechanism of formation of 4-hydroxynonenal during microsomal lipid perodixation; Biochim. Biophys. Acta, 876, 154–156.
14. SUNDBERG R. J.; The Chemistry of Indoles, 1970, Academioc Press.
15. TAYLOR R.; Electrophilic Aromatic Substitution, 1990, J. Wiley & sons, 187.
16. ARCADIA. et al., (1989); Tetrahedron Letters, 30 (19), 2581–2584.
17. SAKAMOTO T. et al., (1986); Heterocycles, 24 (7), 1845–1847.
18. UMEZAWA S. (1939); Bull. Chem. Soc. Japan, 14, 155.
19. B. SHIVARAMA HOLLA and SARVOTTAM Y. AMBEKAR (1978); indian J. Chem., 16B, 240.
20. PENYES J. G. E. (1974); J. Org. Chem. 27, 2614.

We claim:

1. A process for colorimetric assay of 4-hydroxy-2-enaldehydes or of malonic dialdehyde (MDA) alone, as lipid peroxidation indices in an aqueous medium, comprising:

a) addition to the said medium of a reagent chosen from compounds of general formula I below and their addition salts with organic or inorganic bases, or with organic or inorganic acids:

  (I)

in which formula:

A and C, which may be identical or different, each represent H,

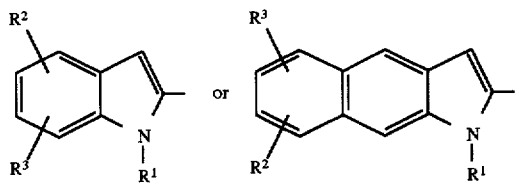

wherein

A and C cannot simultaneously represent H, with:

$R^1$=H; $C_{1-6}$ alkyl; aralkyl with alkyl representing a linear or branched $C_{1-6}$ group; aryl substituted on the aryl ring with one or several groups identical or different, selected from the group consisting of $C_{1-6}$ alkyl, $C_{1-6}$ alkoxy, hydroxyl, amino and carboxyl; alkyl sulfonate, $Y^+$; alkyl phosphonate; $Y^+$; and alkyl carboxylate, $Y^+$;

$R^2$=H; —$OR^4$; F; Cl; Br; I; —$NO_2$; —$SO_3^-Y^+$; —CN; —$COOR^4$; or —$CONR^5R^6$;

—$R^3$=H; —$OR^4$; $NR^5R^6$; —$SR^4$; F; Cl; Br; I; —$NO_2$; —$SO_3^-Y^+$; —CN; —$COR^5$; —$COOR^4$; or —$CONR^5R^6$;

$R^4$=H; $C_{1-6}$ alkyl; aralkyl with alkyl representing a linear or branched $C_{1-6}$ group; or aryl substituted on the aryl ring with one or several groups identical or different, selected from the group consisting of $C_{1-6}$ alkyl, $C_{1-6}$ alkoxy, hydroxyl, amino and carboxyl;

$R^5$=H; $C_{1-6}$ alkyl; aralkyl with alkyl representing linear or branched $C_{1-6}$ group; or aryl substituted on the aryl ring with one or several groups identical or different, selected from the group consisting of $C_{1-6}$ alkyl, $C_{1-6}$ alkoxy, hydroxyl, amino and carboxyl;

$R^6$=H; aryl; aralkyl with alkyl representing a linear or branched $C_{1-6}$ group; or aryl substituted on the aryl ring with one or several groups identical or different, selected from the group consisting of $C_{1-6}$ alkyl, $C_{1-6}$ alkoxy, hydroxyl, amino and carboxyl;

$Y^+$=cation of an organic or inorganic base;

B=

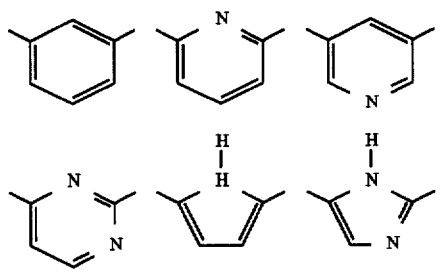

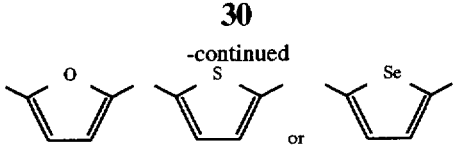

(b) acidification of the medium which has been thus added to, either by an acid selected from the group consisting of carboxylic acids, sulfonic acids, perchloric acid, hydrochloric acid, hydrobromic acid and sulfuric acid;

(c) incubation of the acidified medium at a temperature between 25° and 60° C., for a sufficient period to obtain a stable coloration due to the formation of a chromophoric addition product of the reagent with all the enaldehydes present in the medium or with malonic dialdehyde alone;

(d) measurement of the absorbance of the colored medium at the absorption wavelength which is specific for the chromophoric addition product of the reagent used, and its utilization for determining the enaldehyde concentration, or the concentration of malonic dialdehyde alone.

2. The process according to claim 1 for the colorimetric assay of MDA alone, wherein the acidification is carried out using an acid selected from the group consisting of hydrochloric, hydrobromic and sulfuric acid.

3. Process according to claim 1 further comprising adding a metal salt to the reaction medium.

4. Process according to claim 3, wherein the metal salt is a ferric iron salt.

5. Process according to claim 1, wherein the concentration of previously defined enaldehydes or of malonic dialdehyde alone, depending on the case, is determined using a calibration curve established by means of a standard enaldehyde solution, under the same reaction conditions as the assay to be carried out, by plotting, as a function of the known enaldehyde concentration, the difference of the absorbance A for a given concentration and the absorbance $A_0$ of a control not containing aldehyde, these absorbances being read at the maximum absorption wavelength which is characteristic of the addition product between the enaldehydes as previously defined and the compound of general formula I used.

6. Process according to claim 5, wherein the concentration of enaldehydes sought may be determined from the measurement of the absorbance A of the sample and the measurement of the absorbance $A_0$ made on a control not containing aldehyde and from the molar extinction coefficient E which corresponds to the slope of the calibration straight line, with:

[enaldehyde concentration]=$(A-A_0) \times K/E$, where:

the enaldehyde concentration is expressed in moles.$l^{-1}$;

A and $A_0$ are read with an optical path length of 1 cm and are expressed in cm$^{-1}$;

K is the dilution factor; and

E is expressed in l.moles$^{-1}$.cm$^{-1}$.

7. Process according to claim 1, wherein the compound of general formula I is 1-methyl-2-phenylindole which produces, with enaldehydes, a stable chromophore for which the maximum absorbance wavelength is equal to 586 nm.

8. Requisite or kit for the assay of 4-hydroxy-2-enaldehydes or of malonic dialdehyde (MDA), as lipid peroxidation indices in an aqueous medium comprising:

a) an effective amount of a reagent of general formula I

A and C, which may be identical or different, each represent H,

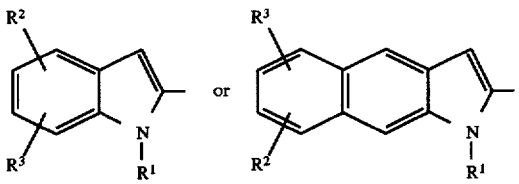

wherein

A and C cannot simultaneously represent H, with:

$R^1$=H; $C_{1-6}$ alkyl; aralkyl with alkyl representing a linear or branched $C_{1-6}$ group; aryl substituted on the aryl ring with one or several groups identical or different, selected from the group consisting of $C_{1-6}$ alkyl, $C_{1-6}$ alkoxy, hydroxyl, amino and carboxyl; alkyl sulfonate, $Y^+$; alkyl phosphonate; $Y^+$; and alkyl carboxylate, $Y^+$;

$R^2$=H; —$OR^4$; F; Cl; Br; I; —$NO_2$; —$SO_3^-Y^+$; —CN; —$COOR^4$; or —$CONR^5R^6$;

$R^3$=H; —$OR^4$; $NR^5R^6$; —$SR^4$; F; Cl; Br; I; —$NO_2$; —$SO_3^-Y^+$; —CN; —$COR^5$; —$COOR^4$; or —$CONR^5R^6$;

$R^4$=H; $C_{1-6}$ alkyl; aralkyl with alkyl representing a linear or branched $C_{1-6}$ group; or aryl substituted on the aryl ring with one or several groups identical or different, selected from the group consisting of $C_{1-6}$ alkyl, $C_{1-6}$ alkoxy, hydroxyl, amino and carboxyl;

$R^5$=H; $C_{1-6}$ alkyl; aralkyl with alkyl representing a linear or branched $C_{1-6}$ group; or aryl substituted on the aryl ring with one or several groups identical or different, selected from the group consisting of $C_{1-6}$ alkyl, $C_{1-6}$ alkoxy, hydroxyl, amino and carboxyl;

$R^6$=H; aryl; aralkyl with alkyl representing a linear or branched $C_{1-6}$ group; or aryl substituted on the aryl ring with one or several groups identical or different, selected from the group consisting of $C_{1-6}$ alkyl, $C_{1-6}$ alkoxy, hydroxyl, amino and carboxyl;

$Y^+$=cation of an organic or inorganic base;

B=

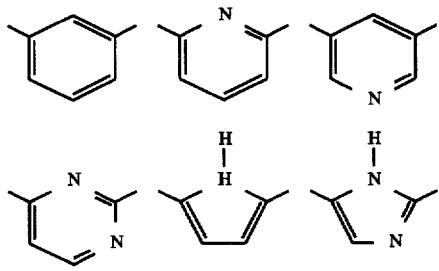

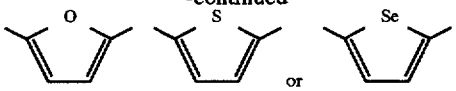

b) at least one acid selected from the group consisting of organic acids and inorganic acids.

9. Requisite or kit according to claim 8 characterized in that it comprises in addition, as reference or standard sample, at least one lipid peroxidation index enaldehyde or one acid-labile precursor for such an enaldehyde, in aqueous or organic solution, at a known concentration.

10. Kit according to claim 8, wherein the organic acid is selected from the group consisting of methane sulfonic acid, trifluoromethane sulfonic acid and trifluoroacetic acid.

11. Kit according to claim 8, wherein the inorganic acid is selected from the group consisting of perchloric acid, sulfuric acid, hydrochloric acid and hydrobromic acid.

12. Kit according to claim 8 wherein each acid is packaged separately.

13. Kit according to claim 8 wherein the concentration of the acid is not lower than 5 moles/l.

14. Kit according to claim 8 wherein the final concentration of the acid in the reaction medium is between 0.5 and 2.5 moles/l.

15. Kit according to claim 8 wherein the final concentration of the reagent in the reaction medium is between 3 and 25 mmoles/l.

16. Kit according to claim 8 wherein the concentration of the reagent is between 5 and 40 mmoles/l.

17. A process for colorimetric assay of 4-hydroxy-2-enaldehyde or of malonic dialdehyde (MDA) alone, or both, as lipid peroxidation indices in an aqueous medium, comprising:

(a) addition to the said medium of a reagent chosen from compounds of general formula I below and their addition salts with organic or inorganic bases, or with organic or inorganic acids:

in which formula:

A and C which may be identical or different, each represent H,

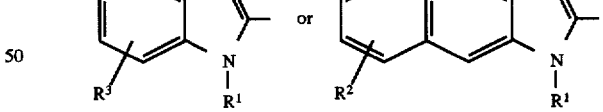

wherein

A and C cannot simultaneously represent H, with:

$R^1$=H; alkyl; aralkyl with alkyl representing a linear or branched $C_{1-6}$ group; aryl substituted on the aryl ring; alkyl sulfonate, $Y^+$; alkyl phosphonate; $Y^+$; or alkyl carboxylate, $Y^+$;

$R^2$=H; —$OR^4$; F; Cl; Br; I; —$NO_2$; —$SO_3^-Y^{30}$ ; —CN; —$COOR^4$; or —$CONR^5R^6$;

$R^3$=H; —$OR^4$; $NR^5R^6$; —$SR^4$; F; Cl; Br; I; —$NO_2$; —$SO_3^-Y^{30}$ ; —CN; —$COR^5$; —$COOR^4$; or —$CONR^5R^6$;

$R^4$=H; alkyl; aralkyl with alkyl representing a linear or branched $C_{1-6}$ group; or aryl substituted on the aryl ring;

R⁵=H; alkyl; aralkyl with alkyl representing a linear or branched $C_{1-6}$ group; or aryl substituted on the aryl ring;

R⁶=H; aryl; aralkyl with alkyl representing a linear or branched $C_{1-6}$ group; or aryl substituted on the aryl ring;

Y⁺=cation of an organic or inorganic base;

B=

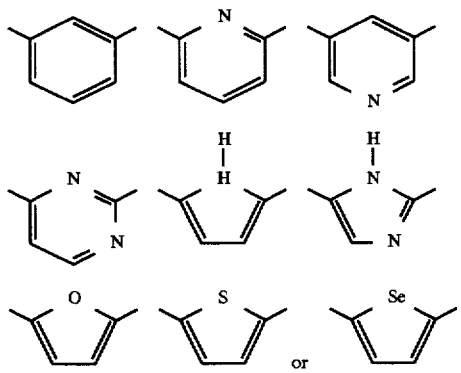

(b) acidification of the medium by an acid selected from the group consisting of a carboxylic acid, a sulfonic acid, a perchloric acid, hydrochloric acid, hydrobromic acid and sulfuric acid;

(c) addition to the acidified medium or an effective amount of a ferric iron salt to promote the yield of formation of a chromophoric addition product of the reagent with all the enaldehydes present in the medium or with malonic dialdehyde alone;

(d) incubation of the acidified medium containing said ferric iron salt at a temperature between 25° and 60° C., for a sufficient period of time to obtain a stable coloration due to the formation of said chromophoric addition product of the reagent with all the enaldehydes present in the medium or with malonic dialdehyde alone;

(e) measurement of the absorbance of the color of the medium at the absorption wavelength which is specific for the chromophoric addition product of the reagent used, and its utilization for determining the enaldehyde concentration, or the concentration of malonic dialdehyde alone or both.

18. The process of claim 17, wherein said aqueous medium is selected from the group consisting of a food product, an enteral nutritive solution, a parenteral nutritive solution and a biological sample.

19. The process of claim 18, wherein said biological sample is selected from the group consisting of whole blood plasma, deproteinized blood plasma, red corpuscle lysates, cerebro-spinal fluid, plasma lipoproteins and solid tissue homogenates.

20. The process of claim 17, wherein the concentration of the reagent in the reaction medium ranges between 3 and 25 mmoles/l, the concentration of the acid in the reaction medium ranges between 0.5 and 2.5 moles/l and the concentration of ferric iron salt in the reaction medium is about 5 µmolar.

21. A compound of general formula I

wherein the definition of formula I is selected from the group consisting of (i), (ii) or (iii) in which:

(i) defines formula I wherein, A and C are identical and are selected from the group consisting of:

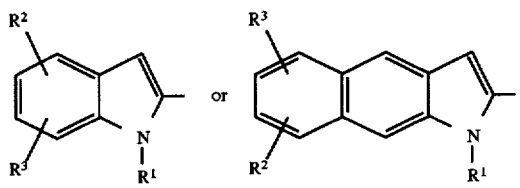

wherein,

R¹=H; a $C_{1-6}$ linear or branched alkyl;
aralkyl with alkyl being a linear or branched group comprising 1 to 6 C;
an aryl substituted on the aryl ring with one or several groups identical or different, selected from the group consisting of $C_{1-6}$ alkyl, $C_{1-6}$ alkoxy, hydroxyl, amino and carboxyl;

R²=H; —OR⁴; F; Cl; Br; I; —NO₂; —SO₃⁻Y⁺; —CN; —COOR⁴; or —CONR⁵R⁶;

R³=H; —OR⁴; NR⁵R⁶; —SR⁴; F; Cl; Br; I; —NO₂; —SO3⁻Y⁺; —CN; —COR⁵; —COOR⁴; or —CONR⁵R⁶;

R⁴=H; $C_{1-6}$ alkyl; aralkyl wherein alkyl is a linear or branched group comprising 1 to 6 carbon; or an aryl substituted on the aryl ring with one or several groups identical or different, selected from the group consisting of $C_{1-6}$ alkyl, $C_{1-6}$-alkoxy, hydroxyl, amino and carboxyl;

R⁵=H; $C_{1-6}$ alkyl; aralkyl wherein alkyl is a linear or branched group comprising 1 to 6 carbon; or an aryl substituted on the aryl ring with one or several groups identical or different, selected from the group consisting of $C_{1-6}$ alkyl, $C_{1-6}$-alkoxy, hydroxyl, amino and carboxyl;

R₆=H; $C_{1-6}$ alkyl; aralkyl wherein alkyl is a linear or branched group comprising 1 to 6 carbon; or an aryl substituted on the aryl ring with one or several groups identical or different, selected from the group consisting $C_{1-6}$ alkyl, $C_{1-6}$-alkoxy, hydroxyl, amino and carboxyl;

Y⁺=cation of an organic or inorganic base; and

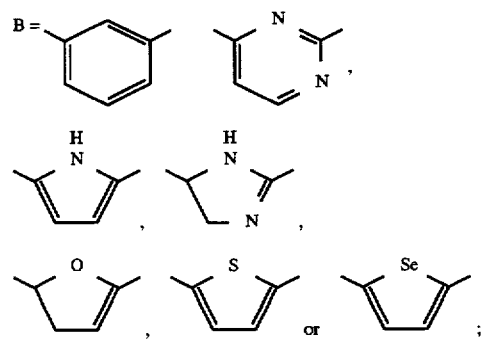

(ii) defines formula I wherein A and C are identical and are selected from the group consisting of:

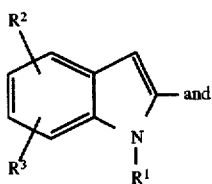

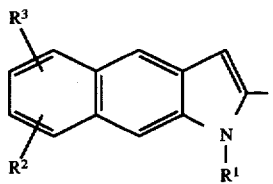

and B=

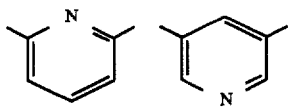

wherein,

R¹=C$_{1-6}$ alkyl; and aralkyl with alkyl representing a linear or branched group comprising 1 to 6 carbons; aryl substituted on the aryl ring with one or several groups identical or different, selected from the group consisting of C$_{1-6}$ alkyl, C$_{1-6}$ alkoxy, hydroxyl, amino and carboxy; C$_{1-6}$ alkyl sulfonate Y⁺; C$_{1-6}$ alkyl phosphonate Y⁺; or and C$_{1-6}$ alkyl carboxylate Y⁺;

R²=H; —OR⁴; —NO$_2$; —SO3⁻Y⁺; —CN; —COOR⁴; or —CONR⁵R⁶;

R³=H; —OR⁴; —NR⁵R⁶; —SR⁴; —NO$_2$; —SO3⁻Y⁺; —CN; —COOR⁴; or —CONR⁵R⁶;

R⁴=H; C$_{1-6}$ alkyl; an aralkyl with alkyl representing a linear or branched C$_{1-6}$ group, or aryl substituted on the aryl ring with one or several groups, identical or different, selected from the group consisting of C$_{1-6}$ alkyl, C$_{1-6}$ alkoxy; hydroxyl, amino and carboxyl;

R⁵=H; C$_{1-6}$ alkyl; an aralkyl with alkyl representing a linear or branched C$_{1-6}$ group, or aryl substituted on the aryl ring with one or several groups, identical or different, selected from the group consisting of C$_{1-6}$ alkyl, C$_{1-6}$ alkoxy; hydroxy, amino and carboxyl;

R⁶=H; C$_{1-6}$ alkyl; an aralkyl with alkyl representing a linear or branched C$_{1-6}$ group, or aryl substituted on the aryl ring with one or several groups, identical or different, selected from the group consisting of C$_{1-6}$ alkyl, C$_{1-6}$ alkoxy; hydroxyl, amino and carboxyl;

Y⁺=cation of an organic or inorganic base; and (iii) defines formula I wherein A and C are different, one of A and C is and the other of A and C is H, wherein, R¹=C$_{1-6}$ alkyl; aralkyl with alkyl being a linear or branched C$_{1-6}$ group; aryl substituted on the aryl ring with one or several groups, identical or different, selected from the a group consisting of C$_{1-6}$ alkyl, C$_{1-6}$ alkoxy, hydroxyl, amino and carboxy; C$_{1-6}$ alkyl sulfonate, Y⁺; C$_{1-6}$ alkyl phosphonate, Y⁺ and C$_{1-6}$ alkyl carboxylate, Y⁺;

R²=H; —OR⁴; F; Cl; Br; I; —NO$_2$; —SO3⁻Y⁺; —CN; —COOR⁴; or —CONR⁵R⁶;

R³=H; —OR⁴; —NR⁵R⁶; —SR⁴; F; Cl; Br; I; —NO$_2$; —SO3³¹ Y⁺; —CN; —COR⁵; —COOR⁴; or —CONR⁵R⁶;

R⁴=H; C$_{1-6}$ alkyl; an aralkyl with alkyl representing a linear or branched C$_{1-6}$ group, or aryl substituted on the aryl ring with one or several groups, identical or different, selected from the group consisting of C$_{1-6}$ alkyl, C$_{1-6}$ alkoxy; hydroxyl, amino and carboxyl;

R⁵=H; C$_{1-6}$ alkyl; an aralkyl with alkyl representing a linear or branched C$_{1-6}$ group, or aryl substituted on the aryl ring with one or several groups, identical or different, selected from the group consisting of C$_{1-6}$ alkyl, C$_{1-6}$ alkoxy; hydroxy, amino and carboxyl;

R⁶=H; C$_{1-6}$ alkyl; an aralkyl with alkyl representing a linear or branched C$_{1-6}$ group, or aryl substituted on the aryl ring with one or several groups, identical or different, selected from the group consisting of C$_{1-6}$ alkyl, C$_{1-6}$ alkoxy; hydroxyl, amino and carboxyl;

Y⁺cation of an organic or inorganic base; and

B =

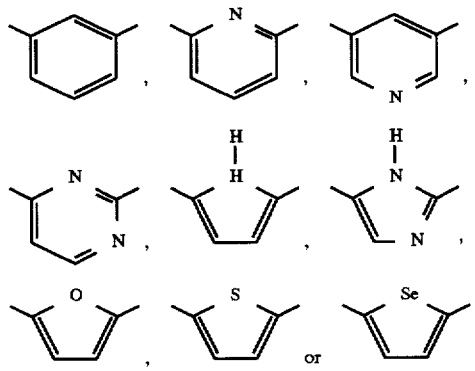

\* \* \* \* \*